(12) United States Patent
Gaharwar et al.

(10) Patent No.: US 11,414,556 B2
(45) Date of Patent: Aug. 16, 2022

(54) NANOCOMPOSITE IONIC-COVALENT ENTANGLEMENT REINFORCEMENT MECHANISM AND HYDROGEL

(71) Applicant: The Texas A&M University System, College Station, TX (US)

(72) Inventors: Akhilesh K. Gaharwar, Cypress, TX (US); David Chimene, Austin, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 0 days.

(21) Appl. No.: 16/493,459

(22) PCT Filed: Mar. 13, 2018

(86) PCT No.: PCT/US2018/022195
§ 371 (c)(1),
(2) Date: Sep. 12, 2019

(87) PCT Pub. No.: WO2018/169965
PCT Pub. Date: Sep. 20, 2018

(65) Prior Publication Data
US 2020/0071550 A1 Mar. 5, 2020

Related U.S. Application Data

(60) Provisional application No. 62/470,727, filed on Mar. 13, 2017.

(51) Int. Cl.
| | |
|---|---|
| C09D 11/101 | (2014.01) |
| B33Y 10/00 | (2015.01) |
| B33Y 70/00 | (2020.01) |
| B33Y 80/00 | (2015.01) |
| B29C 64/118 | (2017.01) |
| A61L 26/00 | (2006.01) |
| A61L 27/02 | (2006.01) |
| A61L 27/16 | (2006.01) |
| A61L 27/22 | (2006.01) |
| A61L 27/26 | (2006.01) |
| A61L 27/50 | (2006.01) |
| A61L 27/52 | (2006.01) |
| A61L 27/54 | (2006.01) |
| A61L 27/58 | (2006.01) |
| C09D 11/03 | (2014.01) |
| C09D 11/04 | (2006.01) |
| C09D 11/107 | (2014.01) |
| B29K 105/16 | (2006.01) |
| B29K 509/00 | (2006.01) |

(52) U.S. Cl.
CPC ........ *C09D 11/101* (2013.01); *A61L 26/0004* (2013.01); *A61L 26/008* (2013.01); *A61L 26/009* (2013.01); *A61L 26/0014* (2013.01); *A61L 26/0023* (2013.01); *A61L 26/0038* (2013.01); *A61L 26/0052* (2013.01); *A61L 26/0057* (2013.01); *A61L 26/0066* (2013.01); *A61L 27/025* (2013.01); *A61L 27/16* (2013.01); *A61L 27/222* (2013.01); *A61L 27/26* (2013.01); *A61L 27/507* (2013.01); *A61L 27/52* (2013.01); *A61L 27/54* (2013.01); *A61L 27/58* (2013.01); *B29C 64/118* (2017.08); *B33Y 10/00* (2014.12); *B33Y 70/00* (2014.12); *B33Y 80/00* (2014.12); *C09D 11/03* (2013.01); *C09D 11/04* (2013.01); *A61L 2300/412* (2013.01); *A61L 2300/418* (2013.01); *A61L 2400/04* (2013.01); *A61L 2400/06* (2013.01); *A61L 2400/12* (2013.01); *B29K 2105/162* (2013.01); *B29K 2509/00* (2013.01); *B29K 2995/006* (2013.01); *B29K 2995/0056* (2013.01); *C09D 11/107* (2013.01)

(58) Field of Classification Search
None
See application file for complete search history.

(56) References Cited

FOREIGN PATENT DOCUMENTS

CN 105238132 A 1/2016

OTHER PUBLICATIONS

Li et al. (Micromachines 2016, 7, 65).*
Mihaila et al. (Adv. Healthcare Mater. 2013).*
International Search Report and Written Opinion for International Application No. PCT/US2018/022195 dated Jun. 29, 2018, 11 pages.
Hong, Sungmin et al., "3D printing of highly stretchable and tough hydrogels into complex, cellularized structures", Advanced Materials, 2015, vol. 27, pp. 4035-4040.
Stevens, Leo et al., 'Ionic-covalent entanglement hydrogels from gellan gum, carrageenan and an epoxy-amine', Soft Matter, 2013, vol. 9, No. 11, pp. 3009-3012.
Bakarich, Shannon E. et al., 'Extrusion printing of ionic-covalent entanglement hydrogels with high toughness', Journal of Materials Chemistry B, 2013, Vo 1.1, No. 38, pp. 4939-4946.

(Continued)

*Primary Examiner* — Patricia Duffy
*Assistant Examiner* — Garen Gotfredson
(74) *Attorney, Agent, or Firm* — Husch Blackwell LLP

(57) ABSTRACT

A biodegradable and biocompatible three dimensional construct comprising a combination of a nano silicate (e.g., laponite) and two different polymers, the two polymers each individually providing at least one covalently linked polymer chain and at least one ionically linked polymer chain, the polymeric chains forming a dual strengthening intertwined polymeric system. The constructs demonstrate improved mechanical and strength properties, while the bioinks provide a material having superior printability characteristics suitable for printing a three dimensional biodegradable construct having an aspect ratio of greater than 2.0. The bioink may also comprise cells or combinations of cells. Methods of using the constructs and bioinks for wound healing preparations and tissue regeneration are also provided.

20 Claims, 14 Drawing Sheets

(56) References Cited

OTHER PUBLICATIONS

Chimene, David et al., 'Advanced bioinks for 3D printing: a materials science perspective', Annals of Biomedical Engineering, 2016, vol. 44, No. 6, pp. 2090-2102.
Chimene, David et al., "Nanoengineered Ionic-Covalent Entanglement (NICE) Bioinks for 3D Bioprinting", ACS Appl. Mater Interfaces Feb. 2018, vol. 10, No. 12, pp. 9957-9968.
Peak et al., *Adv Healthcare Mater* 8:1801553 (2019).
Yue et al., *Biomaterials* 73:254-271 (2015).
Kim et al., *Cell Transplant*, 26:115-123 (2017) (Pub. On line Oct. 7, 2016).
Wilson et al., *ACS Appl Mater Interfaces* 9:43449-43458 (Dec. 2017).
Peak et al., *Langmuir* 34:917-925 (Oct. 2017).
Sears et al., *Adv Healthcare Mater* 1901580 (2020).
Chimene et al., *ACS Applied Materials & Interfaces* 12,14:15976-15988 (2020).
Yue et al., *Biomaterials* 73:254-271 (2015) of record, Highlighted pp. 262 and 264.
*The Merck Index*, 14th ed. O'Neil et al. eds, Merck Research Laboratories, Whitehouse Station, NJ, 2948 Dextran (2006).
Sharma and Sharma, *Trend Biomater Artif Organs* 20(2):000-000(2007).

* cited by examiner

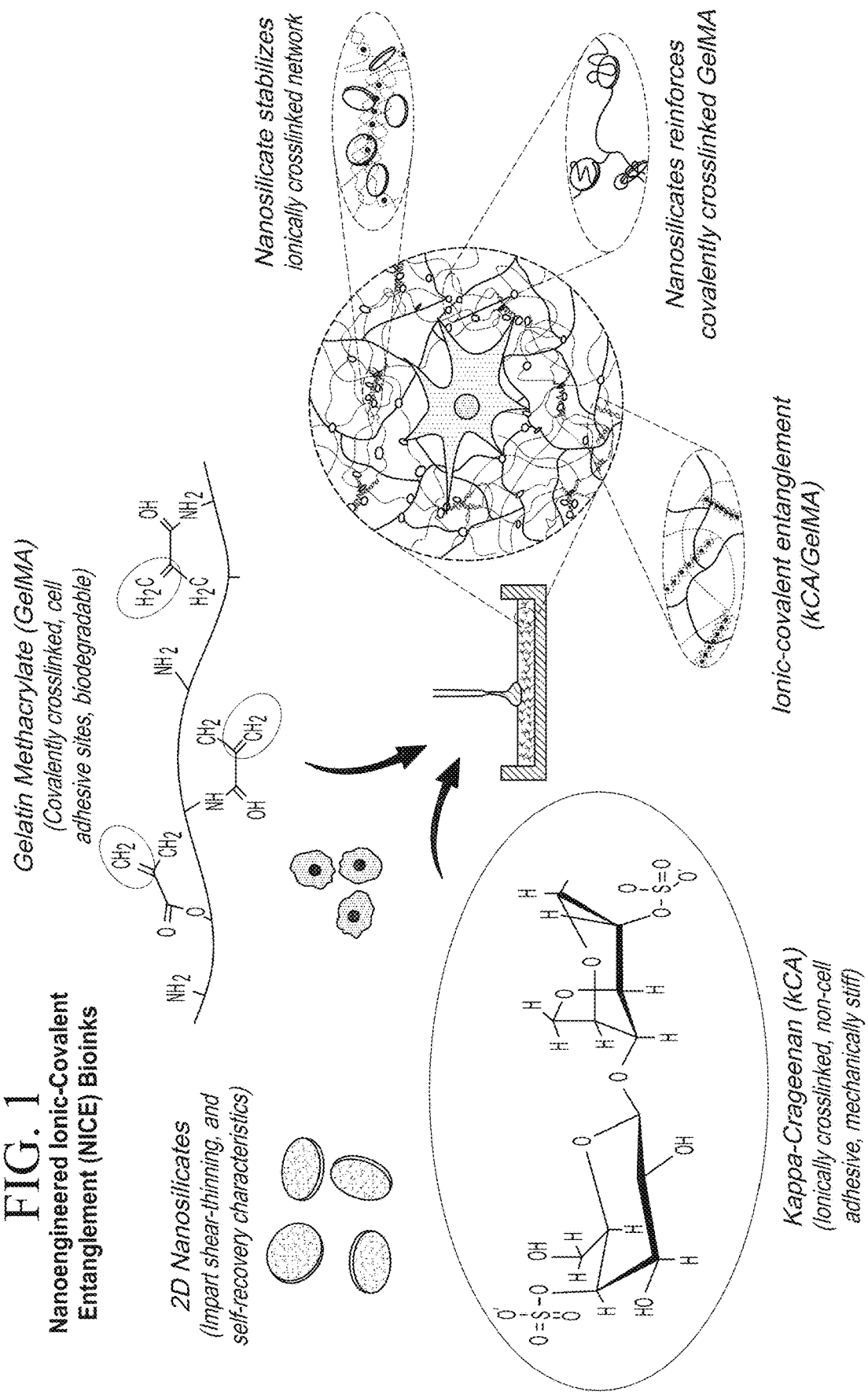

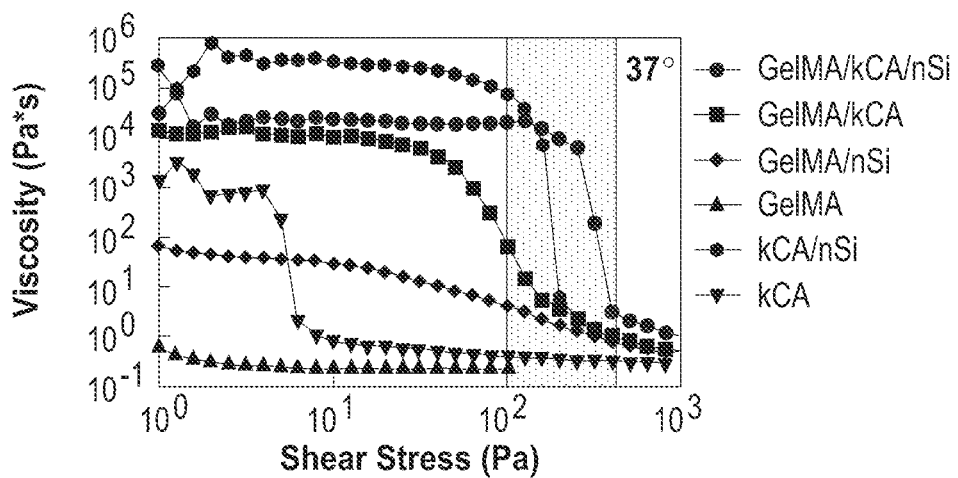
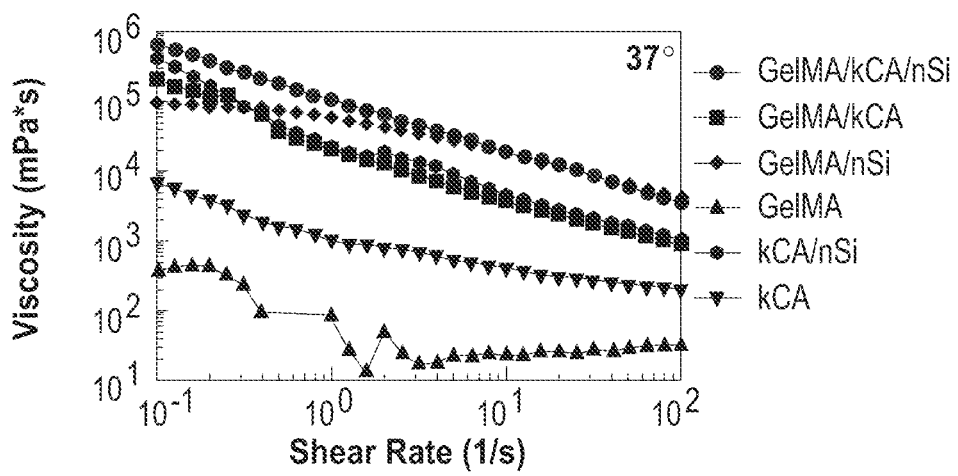
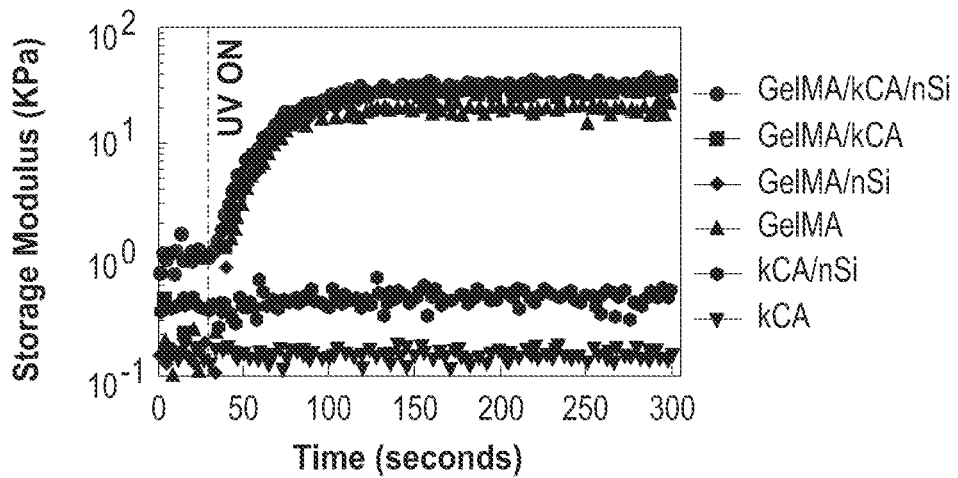
FIG. 2A 3D printed mechanically stiff and elstomeric structures

Controlled Cell Adhesion on Hydrogel Surface (2D seeding)
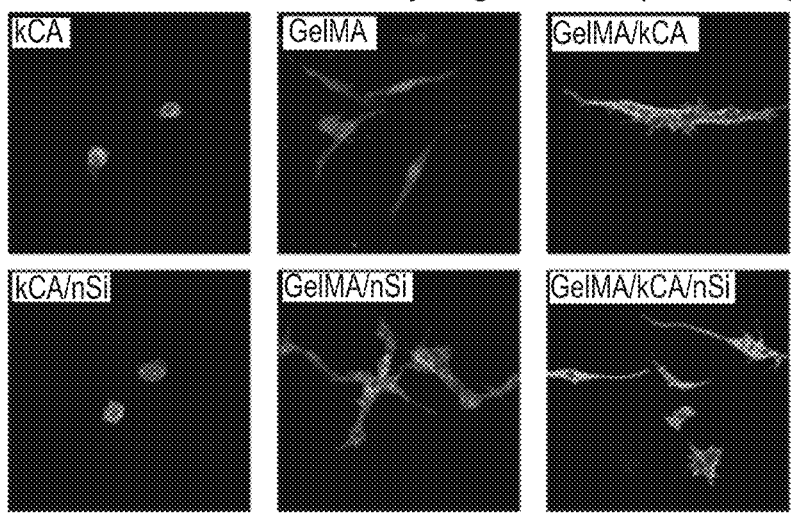
FIG. 4A
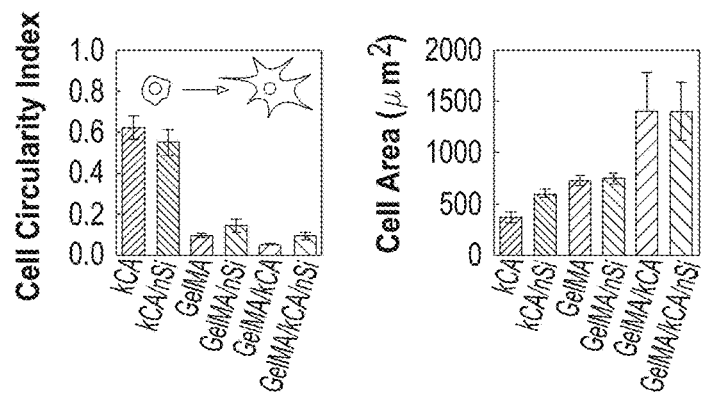
FIG. 4B
Bioprinting using NICE Bioinks
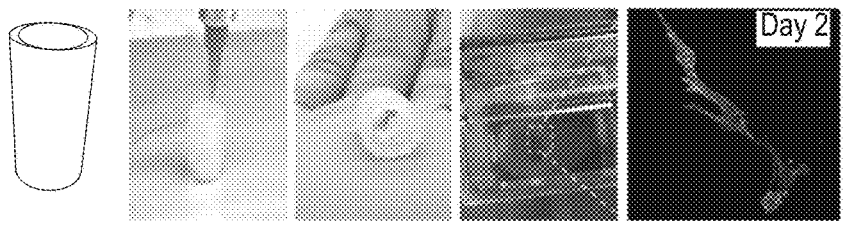
Shear-thinning NICE Bioink Protect Encapsulated hMSCs from Shear Forces
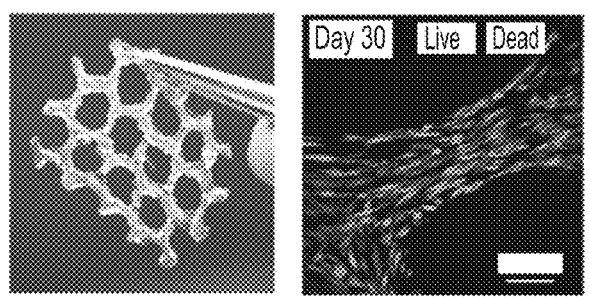
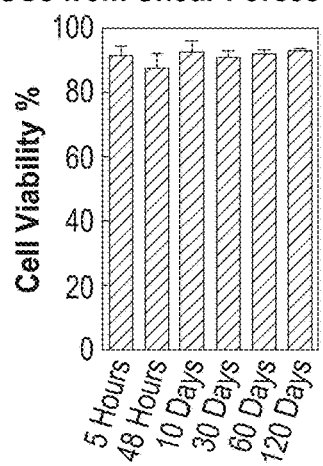
FIG. 4C FIG. 7A    FIG. 7B
STL Designs
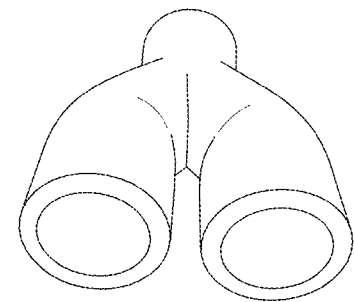 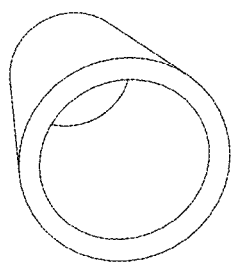
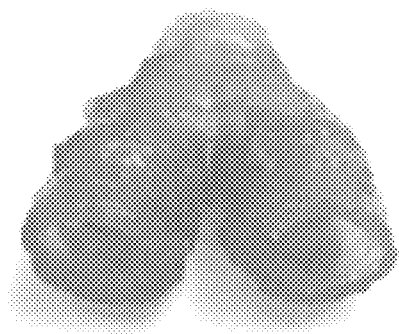 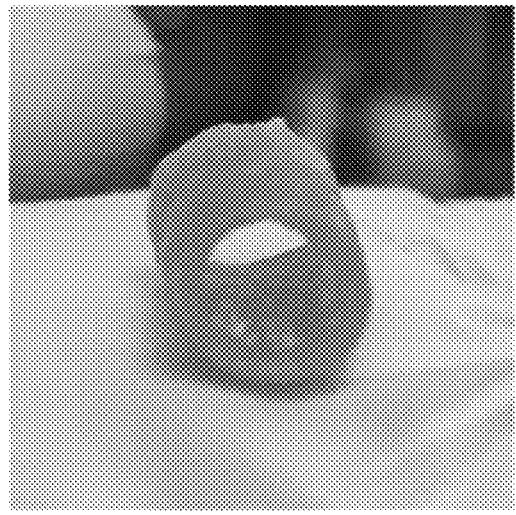
Printed Constructs

FIG. 8A
25°C
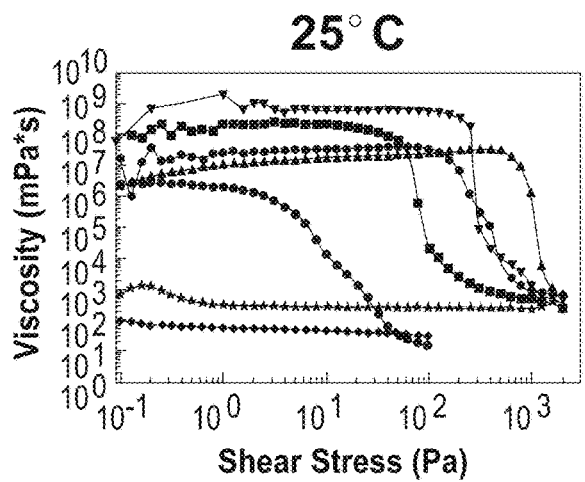
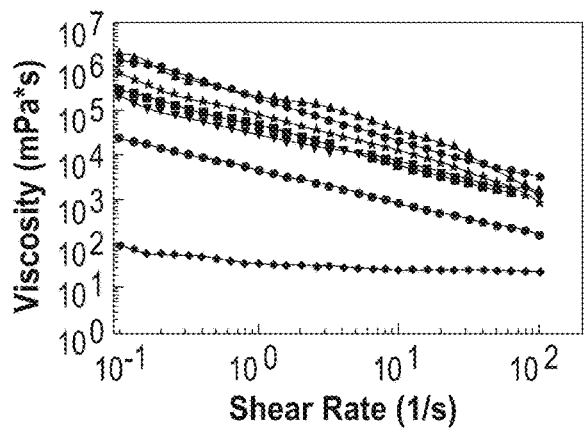
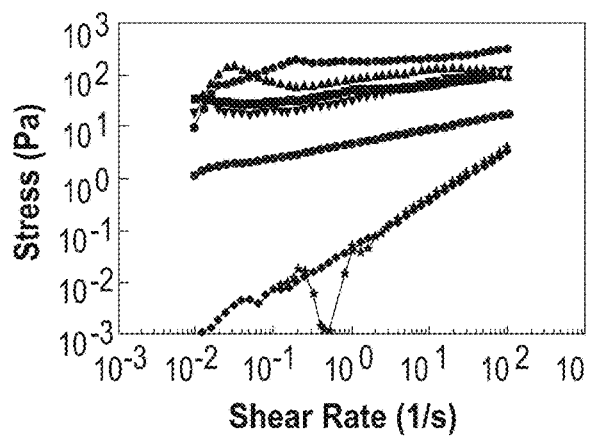
FIG. 8B
37°C
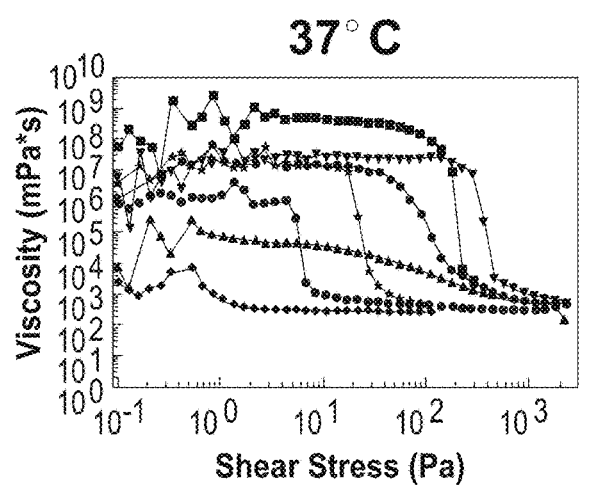
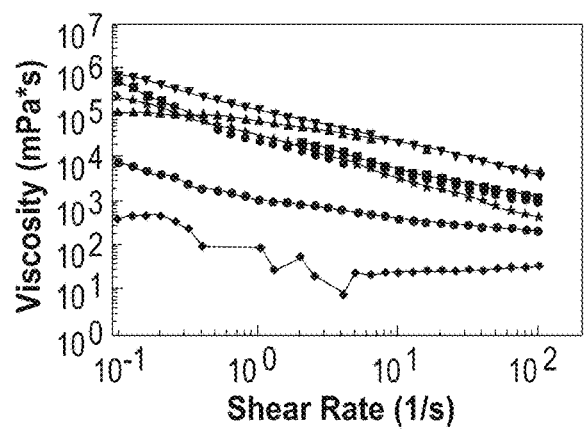
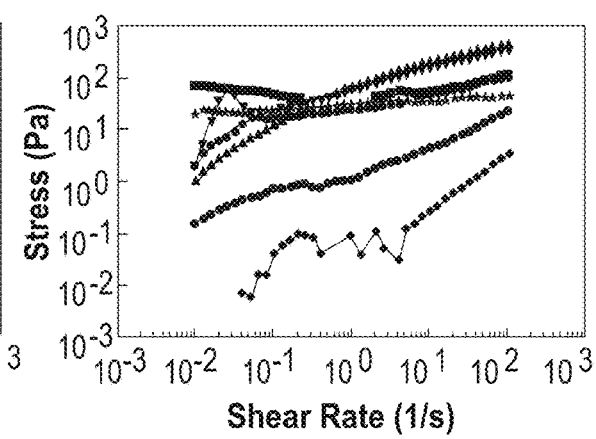
- kCA
- kCA-SiNPs
- GelMA
- GelMA-SiNPs
- GelMA-kCa
- GelMA-kCa-SiNPs
- SiNPs FIG. 9A
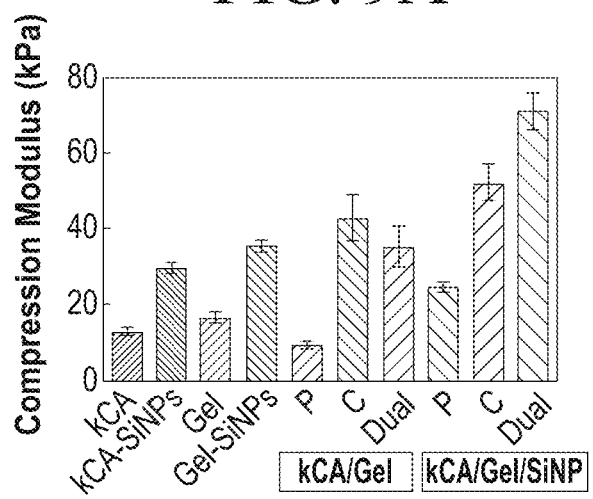
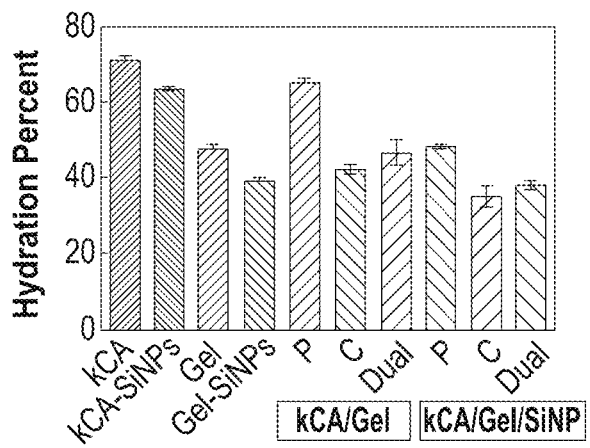
FIG. 9B
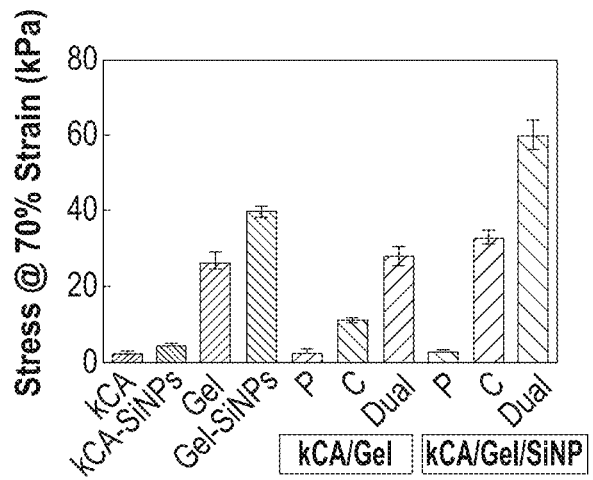
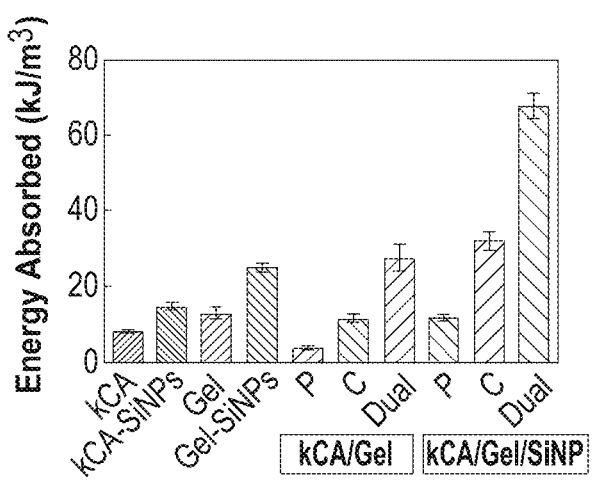

NANOCOMPOSITE IONIC-COVALENT ENTANGLEMENT REINFORCEMENT MECHANISM AND HYDROGEL

STATEMENT REGARDING FEDERALLY SPONSORED RESEARCH OR DEVELOPMENT

This invention was made with government support under CBET1705852 and HRD-1406755 awarded by the National Science Foundation and EB026265 awarded by National Institutes of Health. The government has certain rights to the invention.

TECHNICAL FIELD

This invention relates to the field of biologically compatible materials such as bioinks, and the creation and uses of bioinks in 3-D printing for tissue fabrication and repair.

BACKGROUND ART

3-D bioprinting is emerging as a promising method for rapidly fabricating human biomimetic tissue constructs using cell-containing hydrogels, or bioinks, that are then crosslinked to form a viscoelastic matrix for the encapsulated cells. 3-D bioprinting innovation is driven by the clinical need for creating healthy and functional tissues for integration into a patient's body. However, the field of 3-D bioprinting remains in need of available and more suitable bioinks that are capable of printing structures having sufficient height greater than a few millimeters, as well as materials that more fully accommodate the complex microenvironmental conditions needed for encapsulated cells to accomplish successful long term tissue regeneration. [1-9]

Some bioinks include polysaccharides (like alginate and hyaluronic acid), proteins (including collagen, gelatin, and fibrin), and synthetic polymers (like polyethylene glycol (PEG)). [10] However, while polysaccharides and synthetic polymers are easily characterized and crosslinked, these materials have little-to-no cell-material interaction and poor biodegradability. Natural protein hydrogels have superior bioactivity and are enzymatically degradable, but may be weaker and harder to characterize. Recent efforts in improving available bioink materials have focused on combining the advantages of different bioinks to improve bioactivity, printability, and mechanical strength, often by printing structures containing multiple polymers. These efforts have included functionalizing polymers to add bioactivity, as well as new crosslinking mechanisms and the incorporation of strengthening mechanisms, like nanocomposites, interpenetrating networks, and self healing polymers. [6]

Despite existing developments, most bioinks are still poorly suited to printing 3-D structures. Sufficient printability and strength in a bioink are problems that create challenges in the utilization of 3-D printing in biological/physiological applications for a number of reasons. In particular, conventional bioinks upon extrusion have inferior structural strength when extruded to form layers, and the bioink layers are observed to quickly spread when placed in a multi-bioink layer construct from the weight of additional layers. This problem precludes the formation of clinically useful bioprinted structures that require a height of more than about half a centimeter.

The art of 3-D tissue printing remains in need of materials and methods that, among other things, are suitable for creating taller structures, especially structures having a sufficient height for clinical use. The medical arts remain in need of improved bioinks and improved methods of using these materials that provide for printing of a 3-D structure capable of achieving the formation of a structure having a scaffold aspect ratio capable of sustain the weight of multiple extruded bioink layers without spreading, that provide for the extrusion of a biostructure having a suitable extrusion width, and that provide for the creation of an overall bioink construct that facilitates the diffusion of nutrients sufficient to maintain the viability and growth of cells and tissues, as well as the eventual integration/assimilation of a formed tissue in vivo.

DISCLOSURE OF THE INVENTION

A novel bioink and 3-D biocompatible bioink construct as well as a method for 3D printing and creation of a 3-D biocompatibility construct with the bioink are provided.

In one aspect, the bioink comprises a first covalently cross-linkable polymer and a second ionically crosslinkable polymer, and a silicate nanoparticle (such as Laponite). The bioink may further comprise a pharmacologically acceptable carrier solution, such as water or phosphate buffered saline. The bioink may comprise a gel, a liquid, or a foam preparation.

The bioinks may include nonstructural elements, for example growth factors, proteoglycans, or other biomolecules. These and other nonstructural elements may be included to influence cell behavior, prevent infection, or otherwise conditions that improve the suitability of the materials for particular uses.

The bioink may further comprise cells, such as living cells, including fibroblasts, platelets, stem cells and the like.

The bioink and methods for using the bioinks to fabricate a structure employ a dual strengthening strategy that combines a silicate-nanoparticle, and an ionic and covalent polymeric entanglement mechanism within the same bioink. In some embodiments, the dual strengthening strategy may be described as a dually reinforced nanocomposite ionic-covalent entanglement (NICE) hydrogel bioink structure.

The strengthening mechanisms captured in the present compositions, structures, and constructs with the disclosed bioinks have superior adaptability and utility for the techniques and biotechnologies disclosed here.

The methods disclosed provide superior strength biodegradable compositions and constructs employing a process that is economical. The constructs prepared using the bioinks provide for in vivo cell encapsulation, are cell adhesive, and are enzymatically degradable. The bioink construct in some embodiments are comprised of a series of 2 or more bioink layers, or multiple bioink layers, for example up to 100 layers or more. A construct comprised of the herein described series of bioink layers may be described as having an improved structural integrity, and to impart to the construct an enhanced resistance to spreading.

A method for preparing a construct comprising 2 or more layers, the layers comprising the bioink disclosed herein, employs a 3-D technique with the bioink materials. The present bioinks may be described as having superior printability characteristics. Printability is defined as a bioink's ability to print high aspect ratio structures at a human-relevant scale, and the ability to extrude the desired/intended scaffold or other extruded structure architecture smoothly and at high fidelity. Printability characteristics are also generally described in Bootsma et al. (2016) (Journal of Mechanical Behavior of Biomedical Materials)

In some embodiments, the method may be described as a 3-Dimensional printing method for manufacture of a biocompatible construct. In some embodiments, the method comprises providing a bioink material comprising a nanosilicate material, gelatin, carrageenan, a curing agent and a photo-initiator at room temperature, extruding the bioink material into 2 or more layers to form a multi-layer construct, the construct having an aspect ratio of at least 2, and exposing the multi-layer construct to an ultraviolet light for defined period of time and submerging the UV exposed multi-level construct in a salt solution, such as potassium chloride, for about 30 minutes, to provide a cross-linked multi-layer construct. The construct formed may be described as comprising a multi-layer construct having a dual cross-linking structure with enhanced tensile strength. Other strength metrics are also improved, including compressive strength and toughness. The method provides for extrusion of the bioink with high fidelity, and for the extrusion of layers having an extrusion width of about 200 µm to about 500 µm. In some embodiments, the bioink constructs comprise 2 or more layers, or about 10 or more layers to 95 layers, and a height of about 1 cm to about 2 cm. The method may be created to provide 150 layers/3 cm or more.

The aspect ratio of the bioink constructs provided herein may be described as comprising an aspect ratio of ≥2, or even up to an aspect ratio over 20.

In some embodiments, the bioink may be described as comprising about 10% w/v (80% methacrylated) gelatin methacrylate (GelMa), about 1% w/v kappa carrageenan (KCA), about 2% w/v nanosilicate (such as Laponite), and about 0.25% w/v of a photoinitiator agent, such as ultraviolet curing agent (e.g., Irgacure 2959)

In some embodiments the printable bioink may further comprise cells, such as a cell population comprising live cells, including fibroblasts, platelets, stem cells, and the like. The present constructs are further described as biodegradable constructs. The constructs may be prepared using the bioinks, the bioinks in some embodiments containing live cells. For example, the invention may provide a 3-D printed bioink construct comprising 2 or more overlaying layers, wherein at least some or all of the layers containing live cells. For example, the bioink may be prepared where a population of live cells is added to the bioink prior to extrusion of the bioink to form a layer or other construct. The cell types that may be included in the bioink include, for example, preosteoblasts (for example, MC3T3-E1 cells, a primary osteoblastic cell line), primary cells (for example, stem cells), osteoblasts, chondrocyte-like cells (for example dermal fibroblasts), and the like. Cells included within the bioink may be selected based on the in vivo animal site in which it is to be created and/or placed, or any other relevant criteria specific to the use for which it is intended and/or disease and/or tissue or other defect to be treated. In this way, a particular bioink may be prepared that is designed to maximize the regeneration and/or healing of the particular wound, injury or surgery site into which it is being placed. In these applications, a physiologically compatible solution material, such a phosphate buffered saline (PBS), cell culture media, or other biocompatible, non-toxic solution and/or carrier medium that will maximize the viability of the cell population being included.

In particular embodiments, the bioink, comprises a nanosilicate (such as Laponite), a first covalently linkable polymeric material (such as a gelatin, e.g., methacrylated gelatin) and a second ionically cross-linkable polymer.

The bioinks may further comprise carrageenan.

The method provides for use of the bioink in the extrusion of 2 or more nanolayers (10, 20, 30, 40, 50, 90, 100, 300 layers), stacked upon each other to form a structure having multiple nanocomposite layers. The structure in some embodiments will have a height of about 1 cm to about 6 cm. The stacked nanocomposite layers possess a superior ability to avoid spreading in the stacked configuration, rendering these materials and structures superior to other bioink-created structures that suffer from spreading in a stacked or layered configuration.

Upon extrusion of the bioink to which a photoinitiator has been added, into a desired configuration suitable for the construct desired (such as a series of layers), the construct will be exposed to UV light for an appropriate amount of time sufficient to permit the extruded bioink (such as in an extruded bioink layer) to cure and solidify. The particular UV light intensity and type to be used may be described as exposure to 25 mW/cm2 365 UV light for >10 seconds. Some photoinitiators activate more quickly than Irgacure 2959. Ionic crosslinking may be completed by submersion of the UV-exposed construct/structure into a salt solution, such as a 5% potassium chloride (KCL) solution for >5 minutes. The minimum ionic crosslinking time will vary depending on the size and shape of the bioprinted construct.

Throughout the specification and claims, the following terms take the meanings explicitly associated herein, unless the context clearly dictates otherwise.

The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

As used herein, the term "or" is an inclusive "or" operator and is equivalent to the term "and/or" unless the context clearly dictates otherwise.

The term "based on" is not exclusive and allows for being based on additional factors not described, unless the context clearly dictates otherwise.

The term "a," "an," and "the" include plural references. Thus, "a" or "an" or "the" can mean one or more than one. For example, "a" cell or "a" layer can mean one cell or layer and/or many cells or multiple layers (more than 1, at least 2, etc.).

The meaning of "in" includes "in" and "on."

As used herein, "bioink" refers to a biocompatible, non-toxic material that comprises a methacrylated gelatin component and a silicate nanoparticle component, that is a liquid like material at a temperature of about 37° C. to about 40° C. and a gel-like material at a temperature of less than about 30° C.

As used on the description of the present invention, the term "aspect ratio" is defined as the width of the structure versus the height of the structure. (eg., 1 cm height and 0.05 cm wide has an aspect ratio of 20).

As used in the description of the present invention, the term "silicate nanoparticle" is defined as a silicate particle. The silicate particle is mixed into a solution and allowed to hydrate, then incorporated (i.e., mixed within) the polymer containing material liquid to form the extrudable bioinks.

As used in the description of the present invention, "printability" relates to a bioink's ability to print a high aspect ratio structure at a scale that is useful for animal, including human, use. The printability of a bioink material may also be described as the ability of the material to provide an intended and specific scaffold architecture smoothly and with high fidelity.

As used in the description of the present invention, the acronym "NICE" relates to Nanocomposite Ionic Covalent Entanglement.

The NICE bioink is evaluated against combinations of its component polymers and strengthening mechanisms in order to establish the contributions of each reinforcement mechanism in terms of mechanical properties, cell-material interactions, and printability.

In one aspect, a composition comprising a first covalently crosslinkable polymer (including but not limited to methacrylated peptides, methacrylated hyaluronan, PEGDA), a second ionically crosslinkable polymer (including but not limited to carrageenans, other polysaccharides, alginate (a pH gelling polymer like chitosan), and a nano-silicate, metal oxide, magnetic nanoparticle, or nanocellulose particle. is provided. The composition may further comprise a solvent, such as water, or other physiologically compatible, non-toxic liquid, such as saline.

In some embodiments, the composition comprises a bioink foam. To provide a ready-to-use preparation of the foam bioink, the foam bioink will be combined with an appropriate, non-toxic aqueous carrier/solution (e.g., saline, water, cell culture media), and a photoinitiator, to provide a reconstituted bioink foam. Optionally, and in some embodiments, cells comprising live cells may be added to the reconstituted bioink foam prior to use. In these preparations, the live cells may be described as comprising a population of cells enriched for polymer encapsulated cells.

The nano-silicate component of the preparations may comprise any number of different smectites (such as laponites and montmorillonite). Alternatively, other nanomaterials that could potentially be used apart or in addition to nanosilicates, include metal oxides or magnetic nanoparticles, or nanocellulose.

In some embodiments, the bioink preparations will further comprise a photoinitiator. While virtually any photoinitiator may be used, examples of these materials include Irgacure, lithium phenyl-2,4,6-trimethylbenzoylphosphinate (LAP—this can crosslink under blue light), and VA-086.

In one embodiment, the bioink preparation comprises about 5% to about 15% w/v GelMa (80% methacrylated), about 0.5 to about 4% w/v kappa carrageenan, about 0.5% to about 10% w/v nanosilicate (e.g., Laponite XLG), about 0.1 to about 0.5% w/v photoinitiator (e.g., Irgacure 2959), and a non-toxic, physiologically compatible carrier solution (e.g., water, phosphate buffered saline, or cell culture media).

The constructs prepared with the bioinks of the present invention having a height of about 1 cm to about 6 cm (and an aspect ratio of ≥2, and in some aspect greater than 100). In particular embodiments, the construct has a height of about 3 cm.

Toughness as a characteristic of the present constructs may be described as a material's ability to absorb energy without breaking. This can be tested by mechanically compressing a material with a mechanical tester and recording the total energy absorbed during the cycle. This toughness characteristic is expressed as energy/volume. In FIG. 9, the lower right graph "energy absorbed" is measuring toughness as the gel is compressed by 70% of its initial height. The ICE an NICE networks were also tested with only one network crosslinked (p=physical crosslinked aka ionic crosslinked c=covalent crosslinked) or dual with both ionic and covalent networks crosslinked. As shown in the data at FIG. 9D, there is a significant increase in toughness when both of the polymeric networks are crosslinked.

Regarding NICE versus Methacrylated Kappa (MA-kCa crosslinking alone, the polymer backbone matters as much as the crosslinks. The GelMa, provides an elastic, cell compatible structure, while kappa provides a stiff, brittle structure. Methacrylated kappa behaves like a densely crosslinked single component network, and does not provide for a material having an elastic, cell compatible material. In contrast, the NICE materials are cell compatible and elastic, rendering them superior for use for in vivo applications.

Single component hydrogel networks (like MA-kCa) collapse under stress as cracks concentrate stress and propagate throughout the network. In contrast, ICE networks become tougher by transferring stress between the separate networks, preventing any one zone from being overloaded. The brittle ionic bonds dissipate energy by reversibly breaking their crosslinks, while the flexible covalent network maintains elasticity and prevents crack propagation. Nanosilicates also toughen the network through charge interactions that stabilize the polymer chains, resisting deformation.

Conventional polymeric constructs of methacrylated kappa have no secondary network to allow stress dissipation in the polymer. Instead, polymeric constructs of this polymer collapse, in a manner similar to the collapse observed with single polymer component gels. Conventional multiple crosslinking mechanisms on the same network do not prevent this collapse.

BRIEF DESCRIPTION OF THE DRAWINGS

FIG. 1 shows NICE bioink uses dual reinforcement mechanisms to strengthen the bioink. Ionic-Covalent Entanglement (ICE) of kappa carrageenan and GelMa networks toughens the bioink by dissipating energy through dissociation of reversible ionic crosslinks. Surface charges on nanosilicates form reversible associations with both polymer networks to further strengthen the bioink. This dual reinforcement results in a cell-friendly bioink with greatly improved printability and mechanical strength.

FIG. 2(a) shows Rheology tests and examined the apparent viscosities of the NICE bioink and its components over a range of shear stresses and strain rates, determining the non-crosslinked NICE bioink (GelMa/kCa/nSi) maintains a high yield point and shear thinning characteristics. UV rheology was used to optimize crosslinking time. FIG. 2(b) Shows computer rendered designs for hydrogel structures (UL, middle left), and the same structures as bioprinted using the NICE bioink. The bottom left and right images show additional examples of the elastic nature of the crosslinked bioink. (2(C) SEM images of bioink microstructure show a highly interconnected and porous microenvironment in the NICE bioink (bottom right) ideal for cell habitation, SEM images of component hydrogels are included as a comparison.

FIG. 3B shows compression moduli of bioinks by composition and crosslinking method. FIG. 3C shows the storage modulus of crosslinked GelMa, GelMa-kappa, and GelMa-kappa-laponite (NICE) hydrogels across a range of applied shear stresses (left) and frequencies (right), demonstrating the stability of the materials. FIG. 3D shows hysteresis curves from cyclic compression tests demonstrating the high stiffness and elasticity of the NICE bioink. In FIG. 3D a mechanical compression machine compresses gel to 60% of its original height, then returns to 100%. During the entire cycle, it constantly measures how much force the gel pushes back with. Methacrylated kappa behaves like regular kappa (upper left), the structure collapses so there is no force pushing back on the return cycle. The ICE (bottom center) and NICE (bottom right) have a very "elastic" looking cycle despite containing the same amount of kappa. Note how much more force the gel pushes back with when the nanoparticles are added to the ICE (bottom center versus bottom right). This is the synergistic effect of combining the two strengthening mechanisms. FIG. 3E—The methacrylated kappa would have a low recovery percentage like regular kappa due to its brittle structure; FIG. 3E Left: Total recovery through 5 cycles of compression as calculated from changes in compressive modulus. Right: Energy dissipated in each cyclic compression cycle. FIG. 3F shows a comparison of NICE to available cell supporting bioinks by their mechanical stiffness (compression modulus) and total polymer weight percent within each solution. The following table identifies sources describing the materials used in the study.

| Formulations | Reference |
| --- | --- |
| Agarose | Duarte et al. (2013) |
| Alginate | Chung et al. (2013) |
| Alginate | Chung et al. (2013) |
| GelMA | Bertassoni et al. (2014) |
| GelMA | Bl lllet et al. (2014) |
| PEGDA | Shanjlnl et al. (2015) |
| Alginate-Gelatin | He et al. (2016) |
| Alginate-GelMA | Colosi et al. (2015) |
| Alginate-Gelatin | Chung et al. (2013) |
| PEG-Gelatin | Rutz et al. (2015) |
| Hyaluronic Acid-GelMA | Duan et al. (2014) |
| Hyaluronic Acid-pNIPAAM | Kesti et al. (2015) |
| Alginate-GelMA-PEGTA | Jla et al. (2016) |

FIG. 4A-FIG. 4C. FIG. 4A shows a 3 day culture of 3T3 fibroblasts seeded onto hydrogels illustrating the effect of adhesion ligands on cell behavior. These effects were quantified by calculating average cell area and circularity for each sample. FIG. 4B Bioprinting with NICE bioink. From left to right: model of standard cylinder shape to be printed, bioprinting in process, complete bioprinted structure, incubation of bioprinted structure in media, 3-D encapsulated fibroblasts 48 hours after printing showing cell adhesion and elongation. FIG. 4C 3-D encapsulated 3T3 cells at 30 days demonstrating adhesion, elongation, migration, and proliferation. NICE bioink protects cells during the printing process and provides a remodelable environment suitable for long term cell viability.

Figures 5A, 5B, 5C:
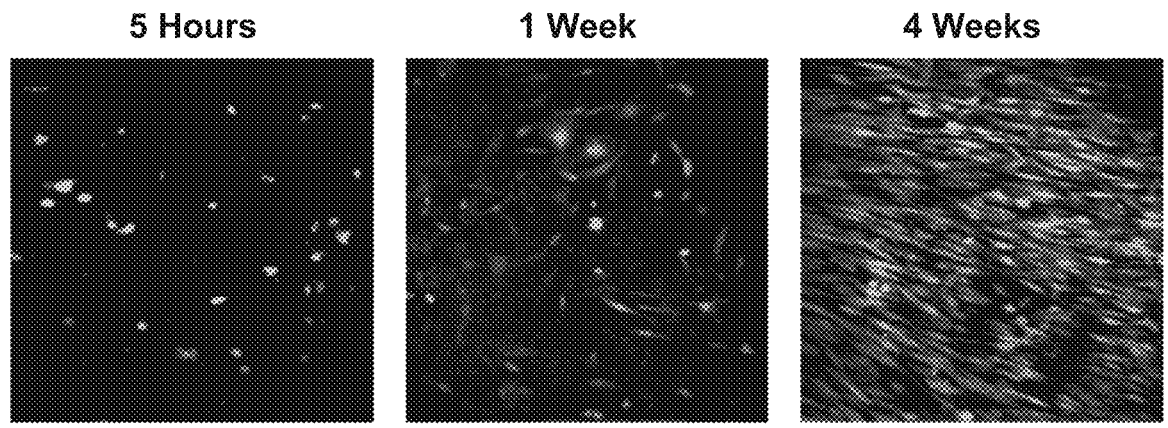

FIG. 5 shows Bioprinted encapsulated 3T3 pre-osteoblasts initially exhibited a round morphology and were evenly dispersed at a density of 5*10$^5$ cells/mL. Cells quickly attached and elongated in their new environment by 1 week, and by 4 weeks had proliferated densely throughout the hydrogel.

Figure 6:
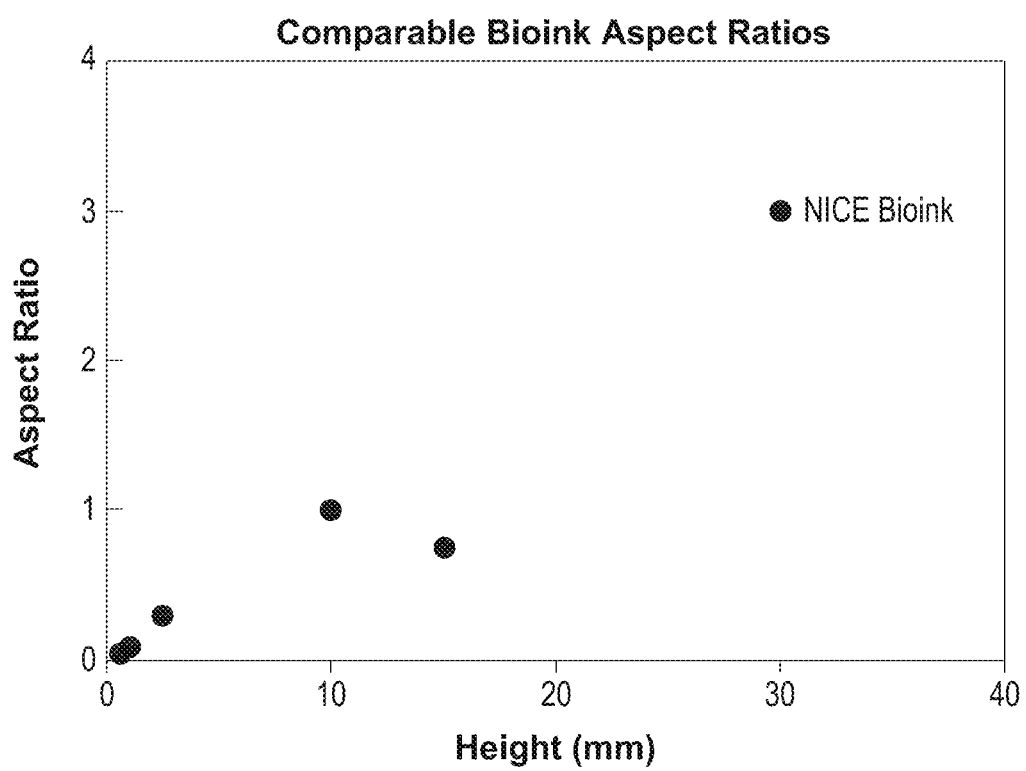

FIG. 6 shows Bioprinted, 3-D Encapsulated Cell Behavior Comparable bioink construct heights and aspect ratios. Comparable results are confined to freestanding bioprinted scaffolds with encapsulated cells that were at least 1 mm tall.

FIG. 7A-7B shows Designs and Printed Structures. Designs for structures were prepared and saved as .stl files then translated into .gcode printer instructions. Bioprinted structures shown in 7A (lower panel) and 7B (upper panel) demonstrate the high fidelity of the prints to software designs and the ability of the NICE bioink to print freestanding human-scale structures. The following table provides references describing the materials used in the present study.

| Formulation | Reference |
| --- | --- |
| Alignate and Gelatin | He et al. (2016) |
| Agarose | Duarte et al. (2013) |
| pNiPAAM and ME-HA | Kesti et al. (2015) |
| GelMa and PEG-X | Rutz etal. (2015) |
| GelMA, Alginate, PEGTA | Jia et al. (2016) |

FIG. 8A-FIG. 8B. FIG. 8A shows Comparison of Rheological Data of Bioinks at 25° C. and 37° C. FIG. 8A shows Rheology tests were conducted at room temperature (25° C.) and body temperature (37° C.) (FIG. 8B) to investigate how the complex interactions between each hydrogel component changed at different temperatures.

FIG. 9 shows Single-Cycle Analysis of Mechanical Properties of Crosslinked Hydrogels. UL: Compression modulus of unconstrained hydrogels of all components (kCa, GelMa, nSi) and crosslinking combinations (Physical, Covalent, Dual). UR: Hydration percent of hydrogels at equilibrium. LL: Stress calculated when unconstrained samples were compressed to 70% strain. LR: Energy absorbed during the entire compression cycle.

Figure 10:
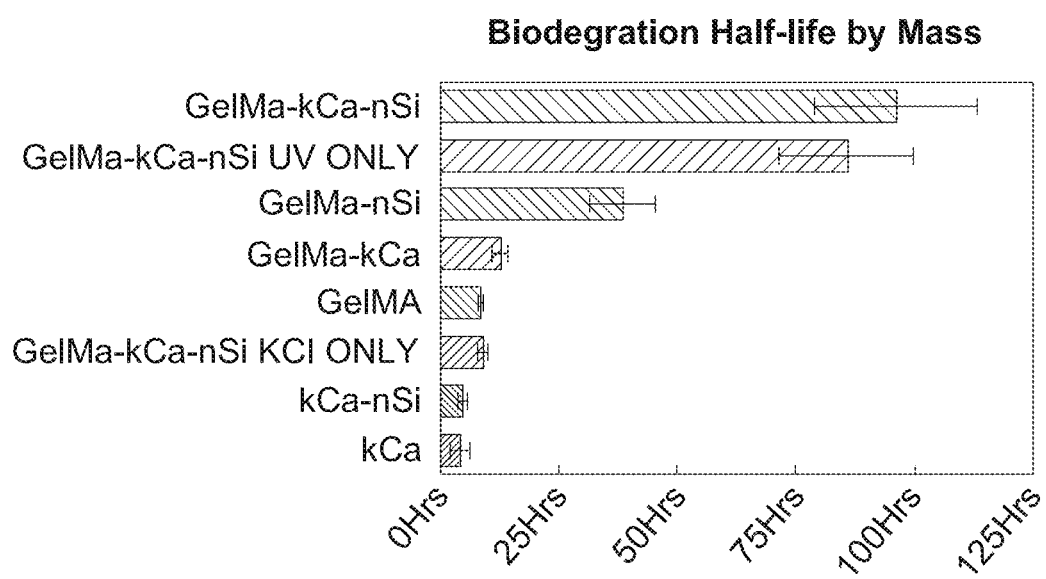
Figure 11A:
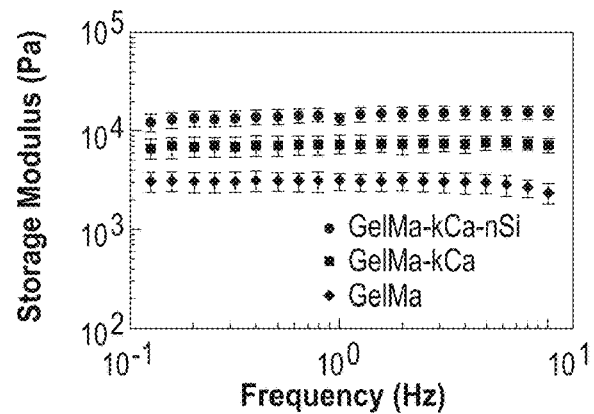
Figure 11B:
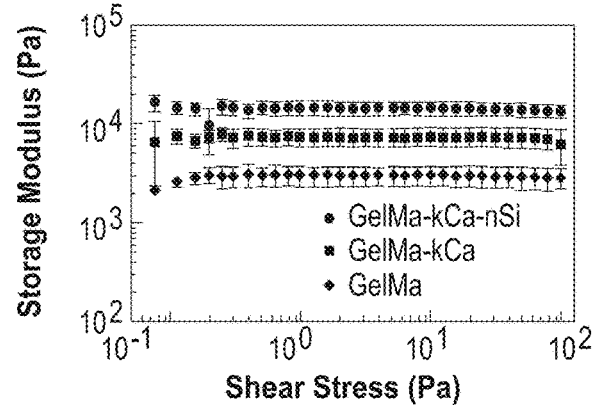
Figure 11C:
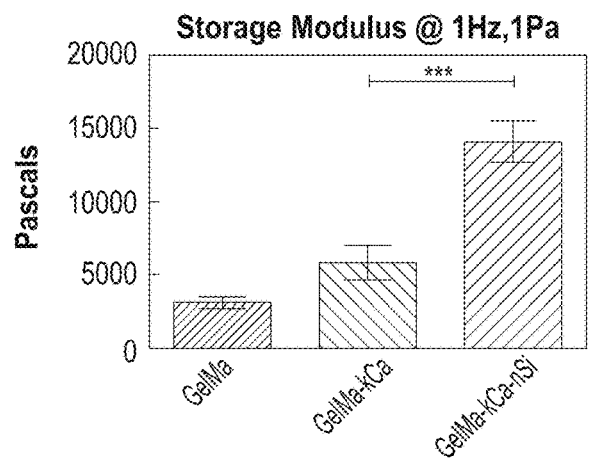
Figure 11D:
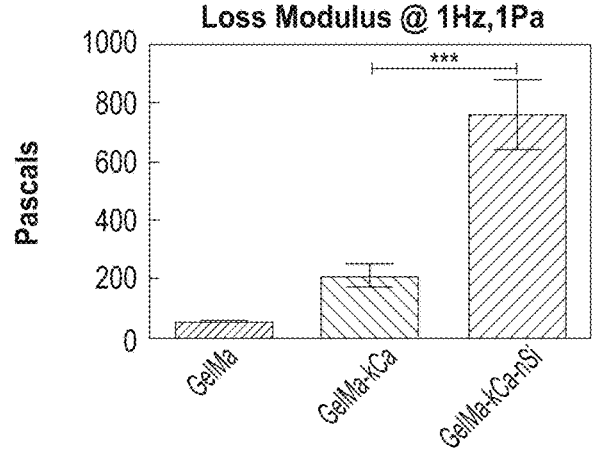

FIG. 10 shows The Biodegradation Half-life of Hydrogels. Crosslinked hydrogels were incubated in PBS with 2.5 u/mL of Collagenase type 2, and mass measurements were recorded regularly. This concentrated collagenase solution dramatically accelerates enzymatic degradation. Time until half of initial mass was lost is recorded here.

FIG. 11 shows Storage and Loss Moduli of Select Hydrogels. Frequency and Stress sweeps were performed to collect storage and loss moduli for crosslinked gels. Results indicate that gels retained their structure throughout both sweeps and that the NICE biolink (GelMa-kCa-nSi) enjoyed significant increases in both storage and loss modulus relative to the other tested gels.

Figure 12:
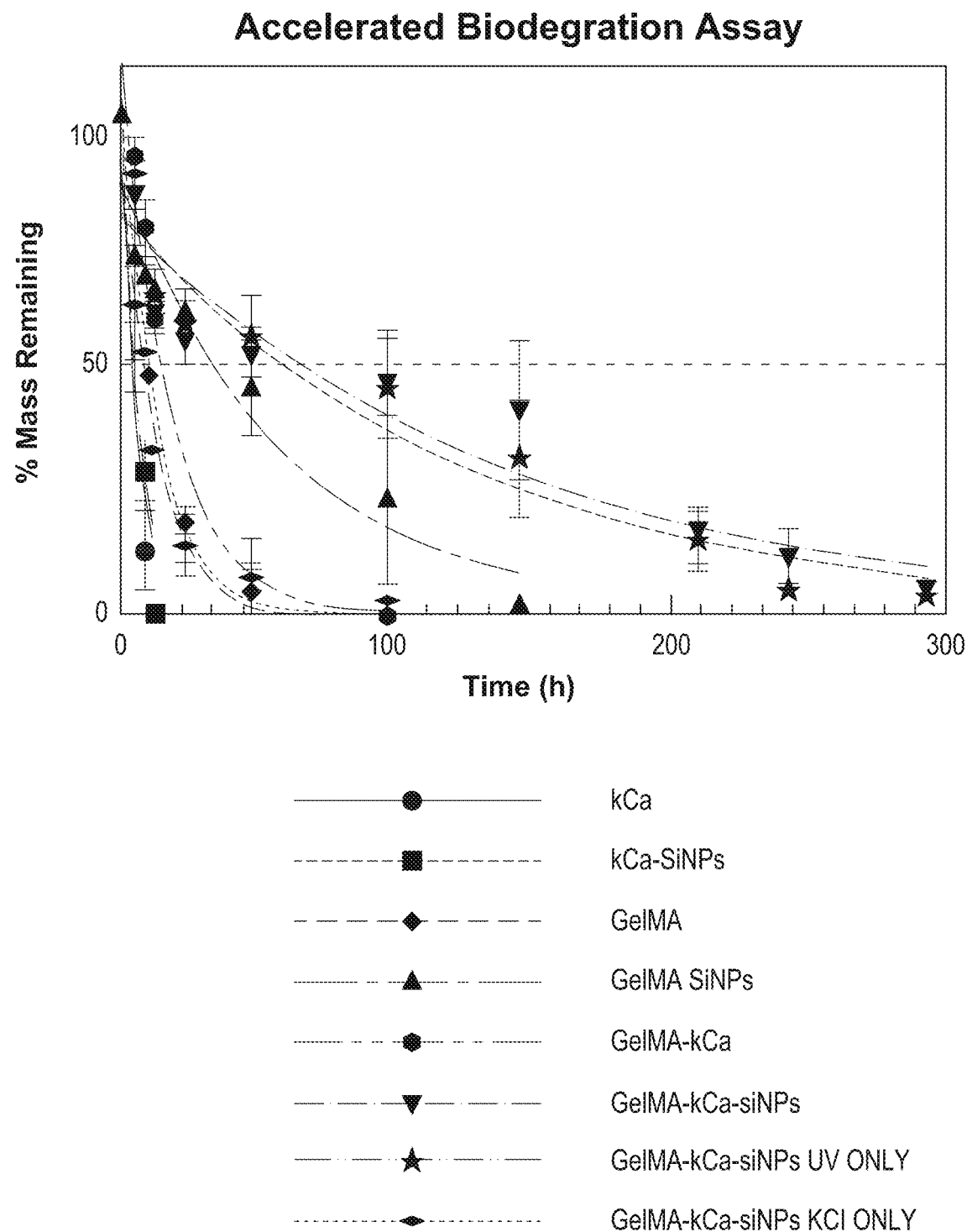

FIG. 12 shows the biodegradation rate of several different bioink scaffolds prepared with the following materials—kCa, kCa-SiNPs, GelMa, GelMa SiNPs, GelMa-kCa, GelMa-kCa-SiNPs, GelMa-kCa-SiNPs UV only, GelMa-kCa-SiNPs KCL only. The biodegradation of constructs prepared with the GelMa-kCa-SiNPs demonstrated the slowest degradation rates, retaining almost about 10% to about 12% mass remaining after 300 hours in the accelerated biodegradation assay used, with those constructs prepared with GelMa-kCa-SiNPs (UV only) providing nearly the same, but slightly faster, degradation (about 8% to about 10% mass remaining after 300 hours).

DETAILED DESCRIPTION OF THE PREFERRED EMBODIMENT

It is specifically intended that the present invention not be limited to the embodiments and illustrations contained herein, but include modified forms of those embodiments including portions of the embodiments and combinations of elements of different embodiments as come within the scope of the following claims.

Example 1—Materials and Methods—Synthesis and In Vivo Integration and Biodegradability The present example describes the bioink composition and synthesis thereof, as well as the use of the bioink in the creation of a multi-layer, 3-D, bioink construct/structure suitable for in vivo and/or clinical use.

Bioink Composition

The NICE bioink was made of 10% w/v (80% methacrylated) gelatin methacrylate, 1% w/v kappa carrageenan (KCa), 2% w/v Laponite XLG, and 0.25% w/v Irgacure 2959 2-Hydroxy-4'-(2-hydroxyethyoxy)-2-methylpropriophenone as a photoinitiator. The nanosilicates (Laponite XLG) were sourced from BYK Additives Inc. The porcine gelatin (gel strength 300, Type A) was obtained from Sigma. Irgacure 2959 and Methacrylic Anhydride were both obtained from Aldrich.

Bioink Synthesis

Gelatin methacrylate (GelMa) was synthesized by dissolving 10 g of gelatin in 100 mL 1× phosphate buffered saline (PBS), then heating for 1 hour at 60° C. After dissolution, 8 mL of methacrylic anhydride was added dropwise over a period of minutes. The solution was kept at 60° C. for 3 more hours, then 400 mL of additional 1×PBS was added. The solution was dialyzed at 50° C. for 7 days, then lyophilized.

The bioink was prepared by 1:1 mixing of 20% w/v GelMa+2% w/v Kappa carrageenan with a solution of 4% w/v Laponite XLG (or other silicate containing agent, such as Laponite XLS, montmorillonite nanoclays, or other smectite nanoclays), 0.5% w/v Irgacure 2959 (or other UVv curing agent, such as VA-086 or LAP). for a final concentration of 10% GelMa, 1% kappa carrageenan, 2% Laponite XLG, and 0.25% Irgacure 2959 w/v. The solution was manually mixed then sonicated using a Fisher Scientific Model 120 Sonic Dismembrator for 2 minutes at 30% amplitude in order to ensure homogenous dispersion of components, stored overnight at 40° C., then allowed to sit at room temperature for 2 days. The NICE bioink's printability depends on storage time and temperature conditions, which should be thoughtfully controlled.

Bioink Crosslinking

The bioink was covalently crosslinked via exposure to 25 mW/cm2 365 nm UV light for 80 seconds. Ionic crosslinking was completed by submersion in 5% potassium chloride (KCl) for 30 minutes. Other salt solutions, such as sodium chloride, calcium chloride, or phosphate buffered saline, may also be used.

Uniaxial Compression

Crosslinked samples were cut into cylinders using a biopsy punch, making sample material cylinders 6 mm in diameter by 2.5 mm thick. Each sample was checked for variance using digital calipers and the ADMET MTEST-Quattro universal testing machine, and variances were factored in to stress and strain calculations. Unconstrained samples were compressed and returned to starting position at 1 mm/minute. Raw data for single cycle compression was processed using an Excel macro for compressive modulus, stress at 70% strain, and energy dissipated. Raw data for multi-cycle compression was processed for compressive modulus, energy dissipated, and recovery using a separate macro. Compression data was taken for hydrogel samples of 10% GelMa, 10% GelMa-2% Laponite, 1% kCa, 1% kCa-2% Laponite, 10% GelMa-1% kCa, and 10% GelMa-1% kCa-2% Laponite. Where applicable, gels were also tested as semi-interpenetrating networks (sIPNs) by crosslinking only one network.

Water Content

Equilibrium hydration was calculated by storing crosslinked gels in PBS overnight and taking their weights, then lyophilizing the gels and comparing dry weight to wet weight. Hydration percentages were calculated using the formula % Hydration=[1-(dry mass/wet mass)]×100

SEM Morphology Visualization

The morphology of the bioink was visualized using scanning electron microscope. Hydrogel samples were frozen in liquid nitrogen, cracked with a razor blade, and lyophilized. Then, the samples were fixed on mounts with carbon tape and sputter coated with gold to a thickness of 21 nm. Samples were visualized using a NeoScope JCM-5000 scanning electron microscope.

Rheology

Rheological testing was carried out on an Anton Paar Physica MCR-301 Rheometer, using a 10 mm PP10 measuring plate and 50 mm CP50-1 measuring plate. Rheometry was used for performing UV gelation, frequency sweeps, stress sweeps, shear stress sweeps, and shear rate sweeps. For UV gelation, each hydrogel's time to gelation was tested by measuring changes in storage modulus while the gels were exposed to 15, 25, or 45 mW/cm2 of 365 nm UV light. Each covalently crosslinkable bioink was tested (n=3) at 10 mm diameter x.5 mm thick. UV light was turned on at 30 s and remained on for 300 seconds.

The frequency sweep was carried out on crosslinked hydrogels at a stress of 1 Pascal (Pa) and covered a range of frequencies from 0.1 Hz to 10 Hz. The stress sweep, also on crosslinked hydrogels, swept a range of shear stresses from 0.1 Pa to 100 Pa at a frequency of 1 Hz.

Finally, stress and shear rate sweeps on non-crosslinked hydrogels were carried out sequentially to measure viscosity under a range of conditions designed to correspond to printing conditions. Shear stress was varied from 0.01 to 2000 Pa. Shear rates from 0.01 to 100 Hz were tested. Gels were kept in a high humidity atmosphere to prevent dehydration from affecting results.

2D Cell Culture & Phenotype Evaluation

To evaluate the hydrogel bioink's ability to culture cells, mouse 3T3 fibroblasts were cultured in vitro on 3.5 cm diameter samples. 3T3 fibroblasts were cultured on hydrogels of 10% GelMa, 1% KCa, 1% KCa+2% Laponite, 10% GelMa+2% Laponite, 10% GelMa+1% KCa, and 10% GelMa+1% KCa+2% Laponite. All cells were used at passage 22 and 100,000 cells were seeded onto each gel sample. Cells were cultured in normal growth media at 37° C. for 3 days. After 3 days, each hydrogel was triple rinsed with PBS, soaked with paraformaldehyde for 1.5 hours, then triple rinsed again. Cells were then permeabilized by exposure to Triton X for 20 minutes and triple rinsed with PBS. 100 μl of phalloidin was added to each well plate, then stored at room temperature for 1 hour. After triple rinsing with PBS, cells were incubated with RNAse for 1 hour at 37° C., triple rinsed again, and incubated with propidium iodide at 37° C. for 20 minutes. Finally, cells were triple rinsed in PBS.

Cells were imaged using confocal microscopy and EZC1 software. Images were taken as Z-stack .ids files, which were compiled into 3-D models using EZC1 software, and compiled into focused 2D images using EZC1 or imageJ via the bioformats import and stack focuser plugins. (60, 79, 81)

Biodegradation

Hydrogel biodegradation rates were assessed to estimate relative degradation rates in vivo and to verify that the NICE bioink is enzymatically biodegradable. 150 mL hydrogels (n=3) were crosslinked and placed in pre-weighed individual containers, then allowed to sit at room temperature overnight in 1×PBS to reach equilibrium. 15 hours later, the solution was replaced with 1×PBS with 2.5 u/mL Collagenase Type 2 (Worthington Biochemical Corporation) and the hydrogels were stored in an incubator at 37° C. The mass of hydrogel remaining was measured by carefully removing all solution from the container, then weighing the hydrogel together with the container. The mass of the jar was subtracted from the measured weight to yield the mass remaining. This procedure kept the weighing process from damaging the hydrogels, which can become fragile as they degrade.

Cell Encapsulation

MC3T3 cell line of Murine preosteoblasts was suspended in the bioink at 37° C. The bioink was prepared using PBS to maximize cell viability. The bioink was then transferred into the extruder and printed into a cylinder with an outer diameter of 1 cm, inner diameter of 0.8 cm, and height of 2 cm. 4 flat disc scaffolds 1 cm in diameter and 1 mm in height were also printed as replicates. All scaffolds were crosslinked using UV light as described above and incubated in media. Live dead imaging was carried out by incubating cells in a PBS solution containing 1 uL/ml calcein AM and 2 uL/ml ethidium homodimer for 1 hour, then soaking once in 1×PBS to limit noise. Imaging was carried out using confocal microscopy.

Bioprinting

Printed shapes were designed in Solidworks and exported as STL files. STL files were loaded into Slic3r to customize printing options and converted into G-code printer instructions. PrOnterface was used to interface with the 3-D printer. Layer height was set to 200 µm, layer width was measured as 500 µm, and print speed was kept at 10 mm/s. When necessary, 2 µl/ml of plumbers tracing dye was added to enhance visualization.

The bioink is stored at 37° C. and loaded into an extrusion tube with a 400 µm nozzle tip and extrusion printed through an 13 RepRap printer. Using these settings, a hollow 2 cm tall×OD 10 mm ID 8 mm cylinder was printed from the bioink. A bifurcated branching blood vessel shape was printed with interior diameter of 5 mm, wall thickness of 1 mm, and height of 1.5 cm.

Cartilage Generation

The bioink gel was also printed directly into a cylindrical defect in the meniscus of a horse. The proximal section of an equine tibia with the attached meniscus was donated by the Texas A&M College of Veterinary Medicine Large Animal Hospital. Using a power drill, a cylindrical defect was introduced into the meniscal cartilage. The tibia section was then held in place on the bioprinter's platform using a cut styrofoam block, and the bioink was printed directly into the cartilage defect in order to reproduce the shape of the missing cartilage. The tibia section was then manually compressed and held inverted to demonstrate the bioink's adhesion to surrounding tissue. The gel was UV crosslinked then exposed to a 5% KCl solution and subjected to repeated manual compressions to qualitatively evaluate resilience and adhesion to surrounding tissue post-crosslinking.

Statistical Analysis

The quantitative experimental results were analyzed and graphed as mean±standard deviation. Statistical analysis of all quantitative data was performed using one-way analysis of variance (ANOVA), and pairwise data comparison was done via Bonferroni's multiple comparison test. Statistical significance was shown as $*p<0.05$, $p<0.01$, and $*p<0.001$.

Example 2—Nanocomposite Reinforcement

The nanocomposite reinforcement was accomplished by inclusion of 2% (w/w) Laponite XLG nanoparticles. Laponite nanoparticles have negatively charged faces and a positively charged rim, which allow Laponite to form reversible electrostatic interactions with the polymer backbones of hydrogels, effectively acting as a weak secondary crosslinker. This interaction can improve stiffness, elasticity, adhesiveness, viscoelastic modulus, and cell adhesion in some hydrogels, and imbue hydrogel solutions with complex shear thinning and bingham plastic behavior (FIG. 1). In the NICE bioink, Laponite forms reversible bonds with both gelMa and k-carrageenan polymers, strengthening the bioink before and after crosslinking, and improving its viscoelastic properties (FIG. 1).[17, 25-31]

Ionic covalent entanglement (ICE) networks are composed of two independent-but-entangled polymer networks that are not crosslinked to each other thanks to distinct crosslinking mechanisms. This is a hydrogel strengthening process that is fast and cytocompatible, unlike conventional dual network strategies, making it well suited for incorporation into the 3-D bioprinting toolkit disclosed here. The increase in strength and toughness from ICE reinforcement is attributed to energy dissipation through reversible disruption of ionic crosslinks, while the more flexible covalently crosslinked network remains intact. This mechanism also allows ICEs to heal disrupted crosslinks under the right conditions and regain mechanical strength over time. In the NICE bioink, the ICE strengthening mechanism was implemented by including 1% (w/w) k-carrageenan, a biocompatible sulfonated polysaccharide that can be ionically crosslinked using KCl under cell-compatible conditions. [15, 18, 32-35]

In 3-D bioprinting, a highly printable bioink must bond tightly to adjacent layers immediately following extrusion and maintain its extruded shape fidelity under the weight of the construct. A bioink must also maintain high cell viability throughout printing and have high water content and porosity to facilitate nutrient diffusion. To recreate functional tissues, however, several additional criteria must be met. For example, the bioinks should enable cells to adhere, migrate, and proliferate within the matrix and exhibit microenvironmental cues to modulate cell differentiation. Finally, the bioink should be proteolytically degradable to allow cells to remodel their environment into functional tissue. As 3-D bioprinting approaches clinical applications, these cell-matrix interactions become critical to success because of the environmental sensitivity of primary cell lines.[1, 4, 6, 8, 9, 12, 36]

To address these requirements, the presently described NICE bioinks based on gelatin methacrylamide (GelMa) (a covalently crosslinkable and enzymatically biodegradable peptide hydrogel that promotes cell adhesion and proliferation), along with the ionically crosslinkable kappa-carrageenan and laponite nanoparticles, were developed. The present NICE bioink was evaluated for all the key characteristics of bioinks: mechanical robustness, printability, and cell-material interactions. Printability was tested by evaluating bioprinted structures and rheological testing to quantify the effects of each bioink component on printability under different conditions. The mechanical properties of the NICE bioink were evaluated to both determine the effectiveness of the strengthening mechanisms and establish a clear picture of the biomechanical microenvironment surrounding the cells. Cell-material interactions of the NICE bioink were investigated in terms of cell viability, cell adhesion, cell morphology, and biodegradability. This approach creates a clear picture of the performance of the NICE bioink in each of the roles required of extrusion bioinks.

Example 3—Blood Vessel 3-D Bioprinting

The printability of the NICE bioink was evaluated through the present studies to illustrate the reproducibility and objectiveness of the material for facilitating direct comparisons with other bioinks. As previously noted, "printability" is defined as a bioink's ability to print high aspect ratio structures at animal (human)-relevant scales and extrude the intended scaffold architecture smoothly and with high fidelity.

Printability of the present methods and materials is demonstrated here with a cylindrical print test of a "blood vessel" shape 1 cm in diameter with 1 mm thick walls (FIG. 4B), approximating the scale of a human blood vessel. This construct can be used as a standard to quantify aspect ratio, maximum construct height, and bioink spreading to allow direct comparison to other bioinks.

Minimizing bioink spreading is necessary for printing high fidelity structures, and was evaluated using the cylindrical print test to a height of 100 layers (2 cm high). The NICE bioink was extruded through a 400 µm diameter tip for a target layer height and extrusion width of 200 µm and 500 µm, respectively. Spreading under the weight of additional layers was quantified by comparing cylinder wall thickness in the lowest 5 and highest 5 layers. Comparison revealed no significant difference in wall thickness between top and bottom layers, demonstrating that the NICE bioink is capable of maintaining print fidelity in structures at least 2 cm tall. Wall thickness measurements remained within 100 µm of 1 mm in all measured points at both ends. Structure height (2 cm) and aspect ratio (20=height/width (2 cm/1 mm)) also agreed with the CAD model within 1 mm, agreeing with the observed lack of bioink spreading. Extrusion performance remained consistent with encapsulated cells and remained stable past 4 months after printing (FIG. 4C). The ability to retain printed shape fidelity at high aspect ratio prior to crosslinking even under stress from 95 additional layers represents a significant advantage over current bioinks, which suffer from layer spreading and cannot print self-supporting structures on this scale.

Example 4—Bioprint of Free-Standing Human Scale Structures

Additional nonstandard prints were performed to demonstrate printing of unsupported overhangs, and the interaction of the NICE bioink with cartilage tissue. A branched blood vessel shape was printed to 1.5 cm high with 5 mm lumen diameter vessels, wall thickness remained at 1 mm (FIG. 7). This shape demonstrated the NICE bioink's ability to print overhangs without external support.

Lumen diameter was chosen to demonstrate the NICE bioink's potential for printing small diameter (<6 mm) blood vessels. This represents a utility of significant clinical need, due in view of the high failure rates of smaller synthetic blood vessels described in the art. [37]

The NICE bioink was also printed directly into a 1 cm defect in an equine meniscus to evaluate gross interactions with the meniscal cartilage. The bioink adhered securely to the surrounding cartilage tissue, remaining in place during manual inversion and compression both before and after crosslinking. This is significant, as adhering and integrating cartilage scaffolds into surrounding tissue has been an obstacle for cartilage repair. This demonstration of cartilage repair in animals supports the use of in situ bioprinting according to the present methods for bioprinting patient-specific cartilage.

The present example and results presented demonstrate that the NICE bioink is highly printable. These techniques may be used to print freestanding 3-D structures over 100 layers (2 cm) tall without crosslinking steps or loss of print-fidelity as measured by the cylinder test, and can print overhanging structures without external support. This is a significant improvement over current bioinks, and is the first example of a bioink capable of printing self-supporting structures on this scale.

Example 5—Rheological Features

Rheological tests performed to explore the mechanism behind this print fidelity in the NICE bioink examined the rheological properties of the bioink components to quantify yield points, shear thinning behavior, and crosslinking kinetics under different conditions (FIG. 3).

Shear stress and shear rate sweeps were run on non-crosslinked bioink components at both room temperature (25° C.) and body temperature (37° C.) to better understand the effects of each component on flow properties at these temperatures (FIG. 3A, FIG. 8). 37° C. is above the gelation point of gelatin, so significant changes in rheology between these temperatures can be expected. Shear stress sweeps at 25° C. showed that bioinks containing Laponite SiNPs had increased apparent viscosity at low shear stresses and sudden, well defined yield points beyond which apparent viscosity decreased quickly to a minimum near the viscosity of the SiNP single component solution. The GelMa-kCa bioink also showed increased apparent viscosity and yield point relative to either single component solution. At 37° C., the rheology of solutions containing GelMa shifted significantly, consistent with prior observations. kCa and kCa-SiNP solutions retained similar apparent viscosities and yield points while the GelMa-SiNP solution showed a drastic decrease in apparent viscosity and yield point. The NICE bioink's apparent viscosity decreased 30-fold without only minimal change in yield point. The SiNP-only solution displayed an increase in viscosity at lower shear stresses relative to its behavior at 25° C. This behavior, along with interactions with kCa, may contribute to the apparent ability of the NICE-bioink to maintain its yield point and printability, even above the gelation temperature of gelMa.

Stress vs shear rate (FIG. 3A, FIG. 8) results indicate that the NICE bioink, as well as all 2-component solutions, behaved as Herschel-Bulkley fluids. The laponite nanoparticle solution notably exhibits bingham plastic behavior at 37° C. but not 25° C. All solutions except GelMa showed a decrease in apparent viscosity as shear rate increased at both 25° C. and 37° C. The shear stress and shear strain sweeps together illustrate the complex interactions of the 3 components of the NICE solution and suggest that the NICE bioink has non-affine flow under printing conditions, which has been shown to improve viability by shielding cells from deformation during extrusion. [39]

Figure 3A:
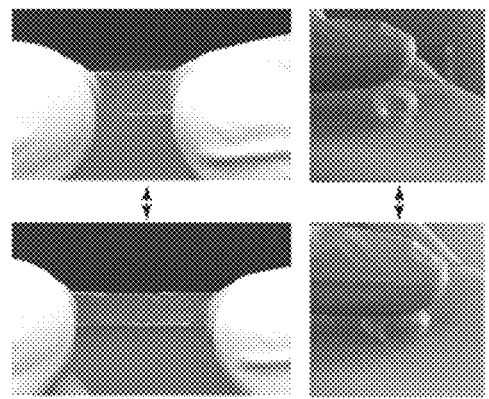
FIG. 3A-FIG. 3F FIG. 3A shows a Visual demonstration of the NICE bioink's mechanical qualities.

UV gelation kinetics showed that exposure to 25 mW/cm^2 of 365 nm UV light solidified gels to 90% of their maximum storage modulus within 80 seconds (FIG. 3A). The inclusion of kCa and laponite nanoparticles did not significantly affect gelation time. This level of exposure to UVA light and the photoinitiator Irgacure 2959 did not result in apparent loss of cell viability during practical tests, and is not likely to cause a significant decrease in cell viability.[40]

The rheology strokes demonstrate that the NICE bioink exhibits a complex rheological profile that can be described as a shear thinning, Herschel-Bulkley fluid that is sensitive to temperature and storage history. The maintenance of a high yield point relative to component gels, along with its viscosity and shear thinning properties, may contribute to NICE bioink's printability. These characteristics point to a non-affine flow that may be responsible for shielding encapsulated cells from damaging stresses during the extrusion process, explaining the observed high cell viability.[9, 12, 39, 41, 42]

Example 6—Mechanical Characteristics

Mechanical experiments were run to isolate the effects of each component of the NICE bioink and evaluate the effectiveness of each reinforcement mechanism.

Initial qualitative results demonstrated that the NICE bioprinted constructs were resilient to compression and tension (FIG. 3A). Uniaxial mechanical compression testing showed that the NICE bioink (71.12+−4.91) had a 4× higher compression modulus than GelMa alone (16.47+−1.45) and 2× higher modulus than either the nanocomposite or ICE alone (35.34+−1.53 and 35.11+−5.23 respectively)(FIG. 3C). This pattern was mirrored in tests of stress at 70% strain (NICE bioink: 301.7+−21.0 kPa) and energy absorbed (NICE bioink: 34+−1.6 kJ/M^3) (FIG. 9). These results confirm that the nanocomposite and ICE reinforcement mechanisms are effective in these bioinks both individually and as combined in the NICE bioink.

Figure 3B:
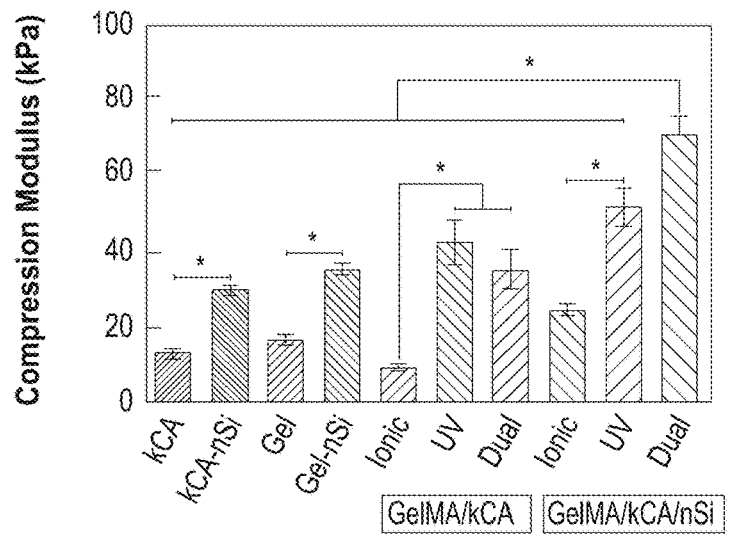
Figure 3C:
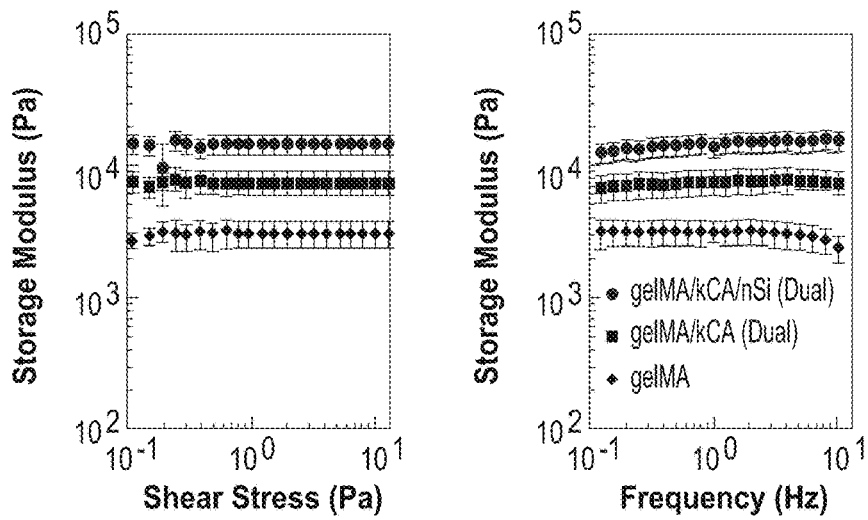
Figure 3D:
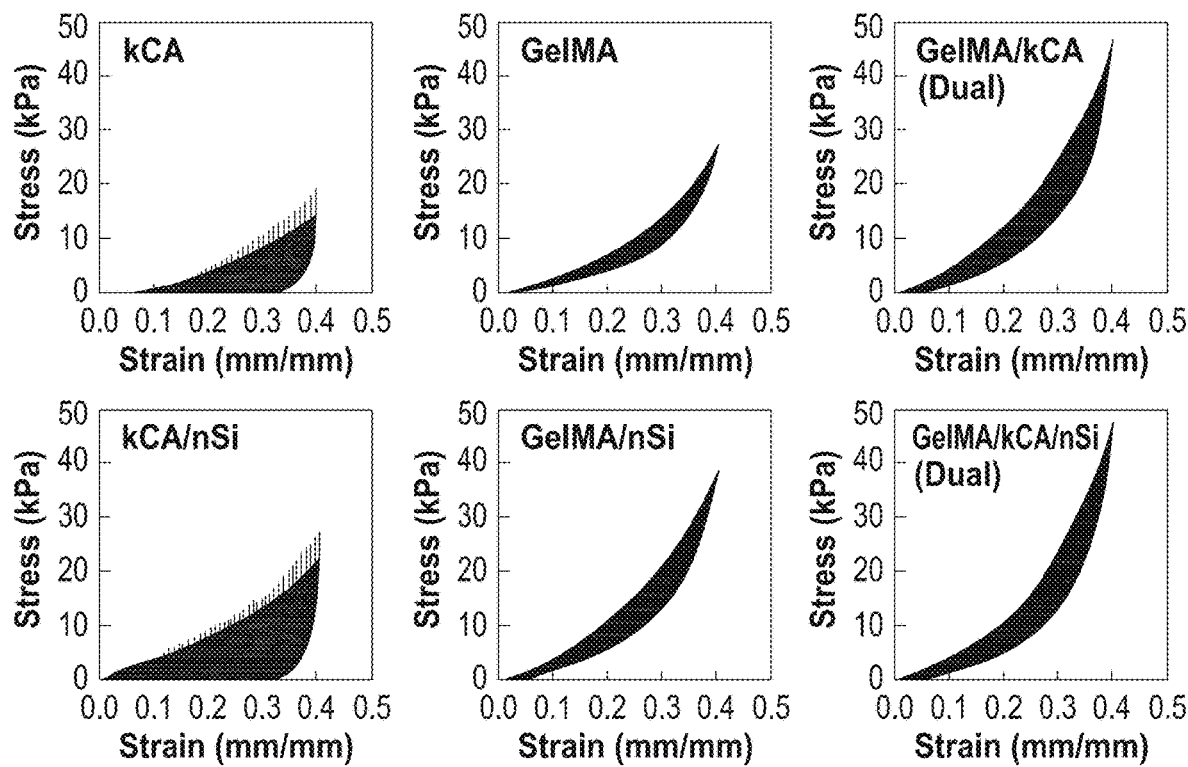
Figure 3E:
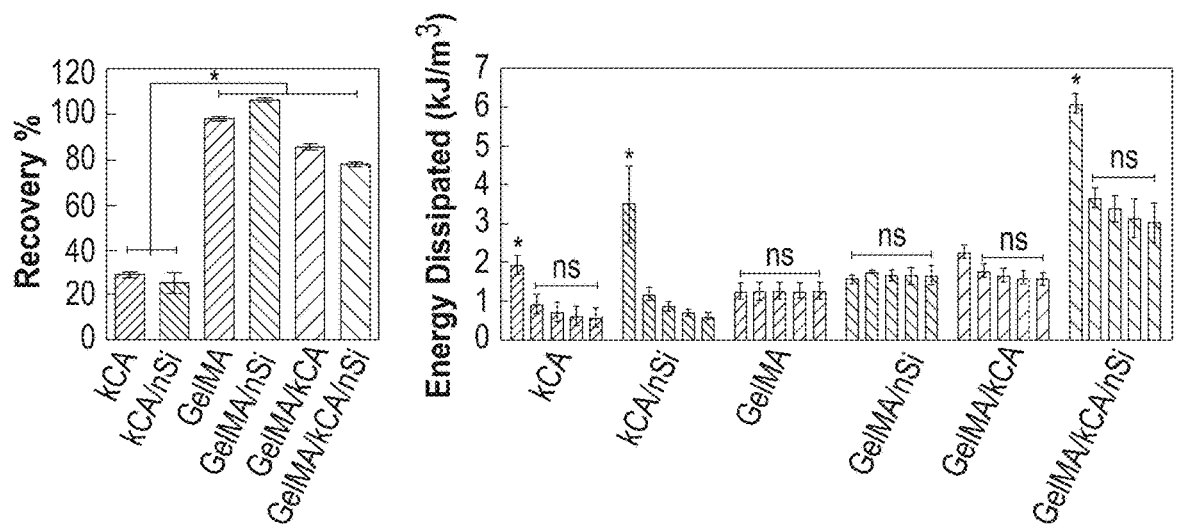
Figure 3F:
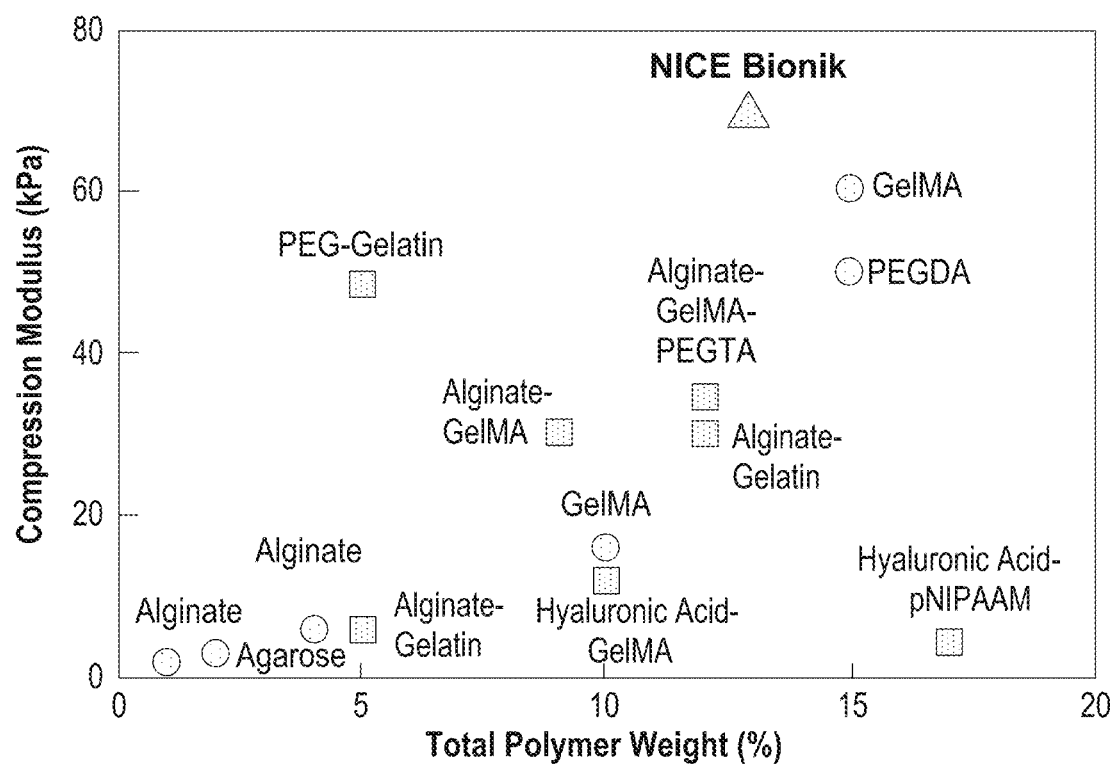

Multi-cycle compression tests evaluated bioink elastic recovery through multiple cycles of strain (FIGS. 3b, 3d). The NICE bioink demonstrated the highest absolute energy dissipation through all 5 cycles (FIG. 3D). By percentage, the NICE bioink had a lower recovery (77%) on the first cycle but similar recovery on subsequent cycles (96-98%).

Example 7—Hydration

Hydration percent calculations (FIG. 9) showed that the GelMa-SiNP nanocomposite and NICE bioink hydration percents were not significantly different (89.81+−0.13% vs 89.50+−0.29%), while the ICE's was slightly higher (91.56+−0.82%). These results show that the improved mechanical properties of the NICE bioink does not appear to be related to an increase in polymer content. Furthermore, the NICE bioink is more highly hydrated than human cartilage (70-85%) and aortic valves (85%), indicating that water content is safely within appropriate physiological range.

Example 8—Porosity and Interconnectivity

Figure 2B:
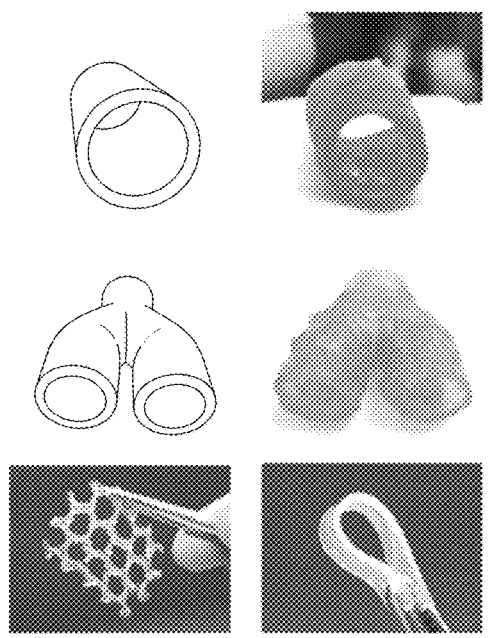
FIG. 2(A)-2(B)

Scanning electron microscope (SEM) images were taken of lyophilized hydrogels in order to measure porosity and interconnectivity and look for changes in the microstructure of the hydrogels caused by the strengthening mechanisms relative to GelMa alone, which is well established as highly cytocompatible. The high levels of interconnected porosity and appropriate pore sizes observed in all covalently cross-linked hydrogels (FIG. 2B) indicate that the hydrogel microstructure can facilitate cell migration. These SEM results support that the reinforcement mechanisms provided in the presently described materials and methods used here are unlike the traditional strategy of increasing polymer content in that they do not decrease the porosity or interconnectedness of the microstructure.[8, 23]

The overall results of the mechanical experiments demonstrated that the NICE bioink enjoys major benefits from both ICE and nanosilicate reinforcement, with compression modulus doubling with each reinforcement mechanism. ICEs and nanosilicate nanocomposites improve the mechanical properties of hydrogels, and these mechanisms can be combined to even greater effect. Furthermore, these benefits remain even under multiple cycles of 40% compressive strain (FIG. 2D), which far exceeds the 10% maximum physiological compression experienced by articular and meniscal cartilage. Finally, hydration calculations and SEM imaging results indicate that the mechanical improvements from the ICE and nanocomposite strengthening mechanisms cannot be attributed to a decrease in hydration degree or porosity. In contrast to the present materials, conventional reinforcement relies on increasing polymer content as a strengthening mechanism.[33, 34, 43-45]

Example 9—Biodegradation Study

The cell-material interactions of the NICE bioink are demonstrated in the present example and are shown to establish the suitability of the present materials/methods for bioprinting. Biocompatibility and bioactivity were evaluated through an accelerated biodegradation assay, cell seeding, and bioprinted cell encapsulation.

Figure 2C:
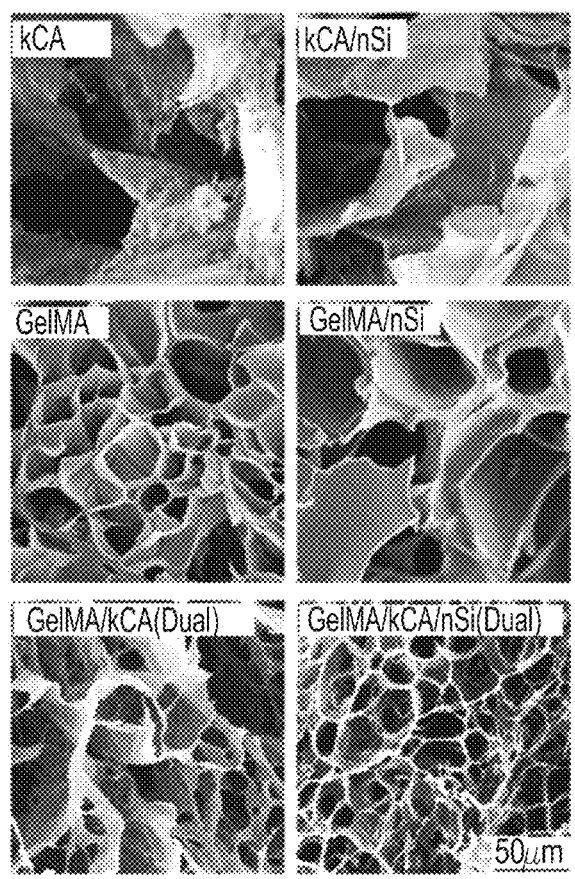
FIG. 2D Accelerated Bioink degradation in PBS/Collagenase solution at 37° C., showing degradation in terms of Mass Remaining (%) over Time.
Figure 2D:
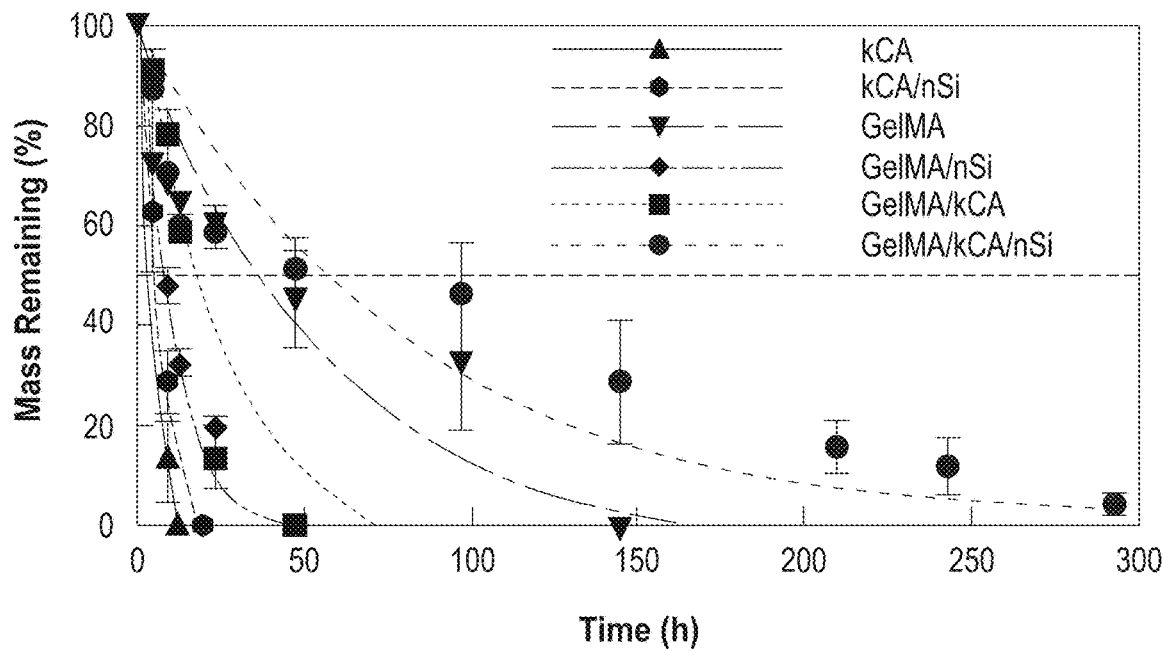

The biodegradation assay was carried out to determine the bioink's susceptibility to enzymatic degradation by repeatedly measuring each hydrogel's mass during incubation in 3 u/mL collagenase type 2 and phosphate buffered saline (FIG. 2C). The inclusion of SiNPs or kCa individually increased resistance to degradation, and the combination of both nanoparticles and kCa in the NICE bioink increased resistance to degradation by about 12 times compared to GelMa alone (96.25+−17.00 hours vs. 8.39+−0.55 hours)(FIG. 10). The ability of the bioink to be degraded by collagenase is vital for long term tissue regeneration because it makes the bioink responsive to cell remodeling behavior.

Next, mouse fibroblasts were seeded onto hydrogel surfaces to evaluate the effects of the different components on cell morphology and size. These 2D cultures revealed that cell circularity depends primarily on the presence of GelMa: fibroblasts on hydrogels containing GelMa elongating significantly while those on kCA or kCa/nSi remained rounded (FIG. 4A). Results also suggested an increase in cell area with ICE hydrogels, though interestingly laponite had no apparent effect on cell area. These results support that cell attachment depends on the adhesion ligands found in GelMa and demonstrates their importance for cell phenotype.

Finally, cells were dispersed within the NICE bioink and bioprinted into 3-D constructs to demonstrate cell viability throughout the bioprinting process and assess cell behavior in the 3-D environment. Pre-Osteoblasts were encapsulated within the NICE bioink and bioprinted into the standard cylinder shape (1 cm diameter, 1 mm wall thickness) to a height of 2 cm (FIG. 4B), as well as several equivalent disk shapes (1 cm diameter, 1 mm thick). Constructs were crosslinked and evaluated for cell viability and morphology over a period of 120 days. Results showed consistently high cell viability (~90%) both immediately after 3-D bioprinting and over the entire 120 day period. Encapsulated cells were observed to adhere, elongate, migrate, and proliferate throughout the entire scaffold (FIG. 5). These cell behaviors, along with long-term cell viability and proteolytic degradation, are vital to successful tissue repair.

The bioactivity results show that the NICE bioink's cell interactions are among the best available in bioinks. The NICE bioink's high modulus, enzymatic degradability, and cell signaling ligands make it much more similar to a native ECM microenvironment than conventional bioinks. This is reflected by the high long term cell viability, adhesion, proliferation, and migration observed within bioprinted constructs, and demonstrates that the NICE bioink is suitable for regenerative medicine bioprinting of tissues and tissue reconstruction, among other things.

Additional studies on NICE bioinks will include using diverse polymers types and concentrations to evaluate the generalizability of the dual strengthening mechanisms and customizing the NICE bioinks for specific tissue types, including hyaline cartilage, fibrocartilage, and bone tissue. Studies are being carried out to evaluate cell differentiation and ECM remodeling within NICE bioinks. These studies will provide for the engineering of complex bioprinted structures containing more robust, bioactive, and printable bioinks Example 10—Bioink Gel in Wound Healing Injectable hydrogels provide can be introduced into a wound to accelerate the healing process and limit scar and adhesion formation. This works by providing a porous environment that cells can migrate through and remodel into natural tissue over time, reducing healing time and minimizing inappropriate scar formation. Current injectable hydrogels on the market can suffer from poor mechanical properties (stiffness, toughness, elasticity), rapid degradation in vivo, low porosity, and low pore interconnectivity. These issues can lead to poor matching with the patient's tissues, delayed healing and increased inflammation. NICE hydrogels are injectable, highly porous (FIG. 2C), encourage cell migration and attachment, and are tough and elastic, making them well suited for wound healing applications. Additionally, nanosilicates have been shown to be an effective drug delivery system by slowly dissociating drug molecules from their surface. This delayed drug release could be used to impregnate the injectable gel with drugs, like antibiotics, or bioactive factors to encourage healing and reduce inflammation.

The NICE hydrogel can be injected into a wound site via syringe, then be quickly crosslinked. Additionally, precrosslinked NICE gels can be applied for wound healing when injection is not necessary, for example as a burn treatment or during conventional surgery. The hydrogel will provide the patient's cells with an extracellular matrix-like environment that they can migrate through and remodel, that is also mechanically robust and enzymatically degradable. The gel can be impregnated with bioactive molecules like growth factors, anti-inflammatories, and antibiotics. The gel can optionally contain encapsulated cells as well.

Example 11—Bioinks as Hemostatic Agents

Hemostatic agents are popularly used in surgery and emergency and military situations to control bleeding. Hemostatic agents work by activating the coagulation cascade, leading to clot formation. However, hemostatic agents can cause downstream clotting at unintended sites, leading to embolisms and stroke.

Nanosilicates have been demonstrated to have clinically significant hemostatic properties in vivo. This effect is suspected to be caused by the nanosilicates concentrating clotting factors. The nanosilicates can be injected as an aqueous solution into a bleeding lesion to significantly reduce clot time. [54]

NICE hydrogels can improve on this model by altering the flow properties of the injected hemostatic, reducing downstream complications. The polymer content of NICE gels significantly reduces the ability of nanoparticles to escape the injection site and flow downstream. The porous nature of the scaffolds enables the nanosilicates to interact with blood clotting components.

Example 12—Bioink Foams and Other Preparations

The NICE bioink may be freeze-dried in order to simplify storage and transport, resulting in a foam that can be rehydrated using an aqueous solution, which may contain cells. This process can be accomplished within minutes because the NICE components are highly hydrophilic. This dehydrated form can rehydrated for use in any of the claims or examples in this document.

BIBLIOGRAPHY

The following references are specifically incorporated herein in their entirety
1. Barker, T. H., Biomaterials, 2011. 32(18): p. 4211-4214.
2. Malda, J., et al., Advanced Materials, 2013. 25(36): p. 5011-5028.
3. Murphy, S. V. and A. Atala, Nat Biotech, 2014. 32(8): p. 773-785.
4. Hunziker, E. B., et al., Osteoarthritis and Cartilage, 2015. 23(3): p. 334-350.
5. Rutz, A. L., et al., Advanced Materials, 2015. 27(9): p. 1607-1614.
6. Chimene, D., et al., Advanced Bioinks for 3D Printing: A Materials Science Perspective. Annals of biomedical engineering, 2016: p. 1-13.
7 Khademhosseini, A. and R. Langer, Nature Protocols, 2016. 11(10): p. 1775-1781.
8. Klotz, B. J., et al., Gelatin-Methacryloyl Hydrogels: Towards Biofabrication-Based Tissue Repair. Trends in biotechnology, 2016. 34(5): p. 394-407.
9. Melchels, F. P., et al., Biofabrication, 2016. 8(3): p. 035004.
10. Carrow, J. K., et al., Polymers for Bioprinting, in Essentials of 3D Biofabrication and Translation. 2015, Academic Press (Eds: James J. Yoo, Anthony Atala). p. 229-248.
11. Kirchmajer, D. M., et al., Journal of Materials Chemistry B, 2015. 3(20): p. 4105-4117.
12. He, Y., et al., Research on the printability of hydrogels in 3D bioprinting. Scientific Reports, 2016. 6: p. 29977.
13. Jabbari, E., et al., Materials Today, 2016. 19(4): p. 190-196.
14. Ozbolat, I. T. and M. Hospodiuk, Biomaterials, 2016. 76: p. 321-343.
15. Bootsma, K., et al., Journal of the Mechanical Behavior of Biomedical Materials.
16. Bakarich, S. E., et al., Journal of Materials Chemistry B, 2013. 1(38): p. 4939-4946.
17. Xavier, J. R., et al., ACS nano, 2015. 9(3): p. 3109-3118.

18. Thakur, A., et al., Nanoscale, 2016.
19. Hoch, E., G. E. Tovar, and K. Borchers, European Journal of Cardio-Thoracic Surgery, 2014. 46(5): p. 767-778.
20. Hoch, E., et al., Journal of Materials Science: Materials in Medicine, 2012. 23(11): p. 2607-2617.
21. Schuurman, W., et al., Macromolecular bioscience, 2013. 13(5): p. 551-561.
22. Billiet, T., et al., Biomaterials, 2014. 35(1): p. 49-62.
23. Yue, K., et al., Biomaterials, 2015. 73: p. 254-271.
24. Van Nieuwenhove, I., et al., Carbohydrate Polymers, 2016. 152: p. 129-139.
25. Pawar, N. and H. B. Bohidar, The Journal of Chemical Physics, 2009. 131(4): p. 045103.
26. Gaharwar, A. K., et al., Advanced materials, 2013. 25(24): p. 3329-3336.
27. Laponite Performance Additives Technical Information B-RI 21, B. Additives&Intruments, Editor. 2014.
28. Gaharwar, A. K., N. A. Peppas, and A. Khademhosseini, Biotechnology and bioengineering, 2014. 111(3): p. 441-453.
29. Chimene, D., D. L. Alge, and A. K. Gaharwar, Advanced Materials, 2015. 27(45): p. 7261-7284.
30. Cross, L. M., et al., Acta Biomaterialia, 2016. 42: p. 2-17.
31. Nojoomi, A., et al., International Journal of Polymeric Materials and Polymeric Biomaterials, 2016: p. null-null.
32. Sun, J.-Y., et al., Nature, 2012. 489(7414): p. 133-136.
33. Matricardi, P., et al., Advanced Drug Delivery Reviews, 2013. 65(9): p. 1172-1187.
34. Stevens, L., P. Calvert, and G. G. Wallace, Soft Matter, 2013. 9(11): p. 3009-3012.
35. Bakarich, S. E., et al., RSC Advances, 2014. 4(72): p. 38088-38092.
36. Gilmore, A., Anoikis. Cell Death & Differentiation, 2005. 12: p. 1473-1477.
37. Seifu, D. G., et al., Nature Reviews Cardiology, 2013. 10(7): p. 410-421.
38. Beddoes, C. M., et al., Hydrogels as a Replacement Material for Damaged Articular Hyaline Cartilage. Materials, 2016. 9(6): p. 443.
39. Aguado, B. A., et al., Tissue Engineering Part A, 2011. 18(7-8): p. 806-815.
40. Mironi-Harpaz, I., et al., Acta biomaterialia, 2012. 8(5): p. 1838-1848.
41. Marquardt, L. M. and S. C. Heilshorn, Current Stem Cell Reports, 2016: p. 1-14.
42. Mouser, V. H., et al., Biofabrication, 2016. 8(3): p. 035003.
43. Kirchmajer, D. M. and M. i. h. Panhuis, Journal of Materials Chemistry B, 2014. 2(29): p. 4694-4702.
44. McNulty, A. L. and F. Guilak, Journal of Biomechanics, 2015. 48(8): p. 1469-1478.
45. Chan, D. D., et al., Scientific reports, 2016. 6.
46. Salamon, A., et al., Materials, 2014. 7(2): p. 1342-1359.
47. An, B., Y.-S. Lin, and B. Brodsky, Collagen interactions: Drug design and delivery. Advanced Drug Delivery Reviews, 2016. 97: p. 69-84.
48. Theocharis, A. D. S., Spyros S Gialeli, Chrysostomi Karamanos, Nikos K, Extracellular matrix structure. Advanced drug delivery reviews, 2016. 97: p. 4-27.
49. Kon, E., et al., Bone and Joint Research, 2013. 2(2): p. 18-25.
50. Lee, V., et al., Tissue Engineering Part C: Methods, 2013. 20(6): p. 473-484.
51. Boere, K. W., et al., Acta biomaterialia, 2014. 10(6): p. 2602-2611.
52. Duan, B., et al., Acta Biomaterialia, 2014. 10(5): p. 1836-1846.
53. Visser, J., et al., Crosslinkable hydrogels derived from cartilage, meniscus, and tendon tissue. Tissue Engineering Part A, 2015. 21(7-8): p. 1195-1206.
54. A. K. Gaharwar, R. K. Avery, A. Assmann, A. Paul, G. H. McKinley, A. Khademhosseini, B. D. Olsen, ACS Nano 2014, 8, 9833.

We claim:

1. A method for manufacture of a three-dimensional biocompatible and biodegradable hydrogel construct, said method comprising: extruding a bioink material that comprises about 1% to about 20% w/v of a first covalently cross-linkable methacrylated gelatin polymer; about 0.1% to about 5% w/v of a second ionically cross-linkable polysaccharide polymer; about 0.1% to about 10% w/v of a nanosilicate; and a photoinitiator present in a pharmacologically acceptable aqueous carrier into layers to form a two or more layer construct, said construct having an aspect ratio of 2 to about 100; exposing the construct to an ultraviolet light for a defined period of time to provide a first covalently cross-linked methacrylated gelatin polymer; and submerging said ultraviolet light exposed construct to a cross-linking salt-containing solution for a period of time to provide a second ionically cross-linked polysaccharide polymer, wherein said first polymer and said second polymer associate to form a dual intertwined polymer network, said dual intertwined polymer network forming said three-dimensional biocompatible and biodegradable hydrogel construct after said cross-linkings.

2. The method of claim 1, wherein the bioink provides for extrusion of a layer having an extrusion width of about 200 mm to about 500 mm.

3. The method of claim 1, wherein said three dimensional biocompatible and biodegradable hydrogel construct comprises 5 layers to 95 layers of said dual intertwined polymer network, and has an aspect ratio of 2.

4. The method of claim 3, wherein the aspect ratio of the three dimensional biocompatible and biodegradable hydrogel construct is more than 2.0.

5. The method of claim 1, wherein said three dimensional biocompatible and biodegradable hydrogel construct comprises two or more layers of said dual intertwined polymer network.

6. A bioink material that comprises a pharmacologically acceptable aqueous carrier that contains about 1% to about 20% w/v of a first covalently cross-linkable methacrylated gelatin polymer; about 0.1% to about 5% w/v of a second ionically cross-linkable polysaccharide polymer; about 0.1% to about 10% w/v of a nanosilicate; and a photoinitiator, said bioink providing a three dimensional biodegradable and biocompatible hydrogel construct after cross-linking.

7. The bioink of claim 6, wherein the nanosilicate is laponite.

8. The bioink in claim 6 further comprising a solvent.

9. A three-dimensional biodegradable and biocompatible hydrogel construct comprising of a series of nano layers, each nano layer comprising a bioink, said bioink comprising a pharmacologically acceptable aqueous carrier that contains about 0.1% to about 10% w/v of a nanosilicate, about 1% to about 20% w/v of a first covalently cross-linkable methacrylated gelatin polymer; about 0.1% to about 5% w/v of a second ionically cross-linkable polysaccharide polymer; said three dimensional structure as extrusion-formed with a height of 200 mm has an aspect ratio of greater than 2 prior to cross-linking, and said bioink providing a three-dimensional biodegradable and biocompatible hydrogel construct after cross-linking.

10. An extrudable gel comprising a hydrogel of the bioink material defined in claim 6.

11. The extrudable gel of claim 10, wherein said pharmacologically acceptable aqueous carrier is water, phosphate-buffered saline, saline or cell culture medium.

12. The extrudable gel of claim 10, wherein said ionically cross-linkable polysaccharide polymer is a carrageenan, alginate or chitosan.

13. A three-dimensional biocompatible and biodegradable hydrogel construct comprising a single layer of a dual cross-linked and interwoven polymer construct that comprises about 1% to about 20% w/v of a first covalently cross-linked methacrylated gelatin polymer, about 0.1% to about 5% w/v of a second ionically cross-linked polysaccharide polymer, and about 0.1% to about 10% w/v of a nanosilicate, said hydrogel construct having an aspect ratio of 2 to about 100.

14. The bioink material of claim 6 further including a photoinitiator.

15. The bioink material of claim 6, wherein said pharmacologically acceptable aqueous carrier is water, phosphate-buffered saline, saline, or cell culture medium.

16. The bioink material of claim 6, wherein said ionically cross-linkable polysaccharide polymer is a carrageenan, alginate or chitosan.

17. The bioink material of claim 6, wherein said ionically cross-linkable polysaccharide polymer is kappa-carrageenan.

18. The bioink material of claim 6, wherein said nanosilicate is a smectite.

19. The bioink material of claim 18, wherein said smectite is laponite.

20. The hydrogel of claim 13 further comprising living cells.

* * * * *